(12) United States Patent
Angelsen et al.

(10) Patent No.: US 7,758,509 B2
(45) Date of Patent: Jul. 20, 2010

(54) MULTIPLE SCAN-PLANE ULTRASOUND IMAGING OF OBJECTS

(76) Inventors: Bjørn A. J. Angelsen, Bugges veg 4b 7051, Trondheim (NO); Tonni F. Johansen, Osloveien 6 7018, Trondheim (NO)

( * ) Notice: Subject to any disclaimer, the term of this patent is extended or adjusted under 35 U.S.C. 154(b) by 1266 days.

(21) Appl. No.: 10/387,775

(22) Filed: Mar. 13, 2003

(65) Prior Publication Data

US 2003/0216646 A1 Nov. 20, 2003

Related U.S. Application Data

(60) Provisional application No. 60/364,747, filed on Mar. 15, 2002.

(51) Int. Cl.
*A61B 8/00* (2006.01)
(52) U.S. Cl. .................. 600/447; 600/459; 600/462
(58) Field of Classification Search .............. 600/437, 600/443, 444, 446, 447, 459, 462, 463, 466, 600/467
See application file for complete search history.

(56) References Cited

U.S. PATENT DOCUMENTS

| | | | |
|---|---|---|---|
| 4,821,731 A * | 4/1989 | Martinelli et al. | 600/463 |
| 5,105,819 A * | 4/1992 | Wollschlager et al. | 600/463 |
| 5,215,092 A * | 6/1993 | Wray | 600/445 |
| 5,398,691 A * | 3/1995 | Martin et al. | 600/463 |
| 5,465,721 A | 11/1995 | Kishimoto et al. | |
| 5,601,084 A * | 2/1997 | Sheehan et al. | 600/450 |
| 5,817,019 A * | 10/1998 | Kawashima | 600/437 |
| 5,906,578 A * | 5/1999 | Rajan et al. | 600/424 |
| 6,149,595 A * | 11/2000 | Seitz et al. | 600/438 |
| 6,171,247 B1 * | 1/2001 | Seward et al. | 600/459 |
| 6,234,968 B1 * | 5/2001 | Sumanaweera et al. | 600/443 |
| 6,276,211 B1 | 8/2001 | Smith | |
| 6,360,027 B1 * | 3/2002 | Hossack et al. | 600/437 |
| 6,482,162 B1 * | 11/2002 | Moore | 600/466 |
| 6,503,204 B1 * | 1/2003 | Sumanaweera et al. | 600/459 |
| 6,572,547 B2 * | 6/2003 | Miller et al. | 600/437 |

(Continued)

FOREIGN PATENT DOCUMENTS

JP 05-161649 6/1993

(Continued)

OTHER PUBLICATIONS

Martin RW, Bashein G, Zimmer R, Sutherland J. An endoscopic micromanipulator for multiplanar transesophageal imaging, Ultrasound in Medicine and Biology, Dec. 1986 12(12), pp. 965-975.*

(Continued)

*Primary Examiner*—Brian Casler
*Assistant Examiner*—Amanda Lauritzen
(74) *Attorney, Agent, or Firm*—Cohen Pontani Lieberman & Pavane LLP

(57) ABSTRACT

A method of real time ultrasound imaging of an object in at least three two-dimensional scan planes that are rotated around a common axis, is given, together with designs of ultrasound transducer arrays that allows for such imaging. The method is also introduced into a monitoring situation of cardiac function where, combined with other measurements as for example the LV pressure, physiological parameters like ejection fraction and muscular fiber stress is calculated.

31 Claims, 21 Drawing Sheets

U.S. PATENT DOCUMENTS

| | | | |
|---|---|---|---|
| 6,607,488 B1* | 8/2003 | Jackson et al. | 600/443 |
| 6,685,644 B2* | 2/2004 | Seo et al. | 600/447 |
| 2003/0065265 A1* | 4/2003 | Jackson et al. | 600/443 |
| 2003/0214379 A1* | 11/2003 | Satoh et al. | 336/200 |
| 2005/0119572 A1* | 6/2005 | Angelsen et al. | 600/443 |
| 2005/0203396 A1* | 9/2005 | Angelsen et al. | 600/437 |
| 2006/0034513 A1* | 2/2006 | Cai et al. | 382/173 |
| 2006/0036176 A1* | 2/2006 | Angelsen et al. | 600/459 |
| 2007/0055150 A1* | 3/2007 | Donaldson et al. | 600/437 |
| 2007/0238999 A1* | 10/2007 | Specht | 600/437 |

FOREIGN PATENT DOCUMENTS

JP 08-000627 1/1996

OTHER PUBLICATIONS

Summary Journal Article S.I. Rabben, F. Irgens, and B. Angelsen, Heart Vessels vol. 14, No. 4, Jul., 1999.

English language translation of Japanese Publication No. JP 05-161649.

English language translation of Japanese Publication No. JP 58-004540.

* cited by examiner

MULTIPLE SCAN-PLANE ULTRASOUND IMAGING OF OBJECTS

PRIORITY CLAIM

Priority is claimed for this invention and application, corresponding application(s) having been filed in US on Mar. 15, 2002, No. 60/364,747.

BACKGROUND OF THE INVENTION

1. Field of the Invention

The present invention is directed to real time ultrasound imaging of an object, like a biological structure, in multiple scan planes. Designs of efficient ultrasound phased array bulk wave transducers for two-dimensional ultrasound imaging, with several, electronically selectable 2D scan planes, are given. The electronic selection of the 2D scan plane direction allows so rapid switching of the direction that practically real time observation of moving objects like the heart, can be obtained simultaneously in several scan planes. The invention also addresses real time ultrasound monitoring of the cardiac function.

2. Description of the Related Art

In medical ultrasound imaging, one often examines an object through a variety of two-dimensional (2D) scan plane directions to observe the form, regional variations, and volume of the object. In particular one uses such multiple scan plane imaging of the heart to assess regional variations in the wall motion and myocardial contraction/relaxation, as well as to calculate the time varying volume of the heart, or the temporal variation of the fiber stress and strain in the heart. Other situations are observations of fetuses, tumors, etc., especially for calculating the volume to study growth.

In practical clinical examinations, such multiple 2D scan planes are generally obtained through manual movement of the 2D ultrasound probe, where for example with transesophageal measurements of the heart with a 2D phased array probe, special mechanisms have been designed for rotation of the ultrasound array through remote control. A phased array transducer for electronic selection of the ultrasound scan planes in two angular directions has been presented in [1], but this solution has found limited practical use, mainly because one wants to observe the object in more than two planes, generally at least three or four angular directions of the 2D scan plane.

The present invention presents a solution to this problem, with the design of a phased array transducer that allows free electronic selection of the 2D scan plane in more than 2 angular directions, for example 3 or 4 angular directions.

SUMMARY OF THE INVENTION

The invention presents methods for practically real time ultrasound imaging of objects in 3 or more 2D ultrasound scan planes, where the 2D scan-planes are rotated around a common axis. With practically real time is here meant that the image data is collected along a set of sample beams within said 2D scan planes, and the sample beam data collection occurs so frequently of the object that all the sample beam data defining the image is collected within so short time period in relation to movements of the object, that the collected data captures a for practical purposes frozen frame the moving object. The image data can in addition be displayed on an image screen with so slow delay that one for practical purposes can view the object as it moves.

Such multiple 2D real time imaging is useful to study regional variations in cardiac wall motion. Using image analysis for automatic selection of the edges of for example a heart cavity or a tumor, one can study dimension and volume variations of the object to study tumor growth or ventricular volumes and ejection fraction. Based on ventricular dimensions, one can calculate myocardial strain, and with Doppler analysis one can quantitate regional wall velocity and strain velocity of the myocardium in each beam direction. Doppler analysis can also be used with forced deformation of tissue to study regional variations in tissue elasticity with methods referred to as elastography. With added input of the left ventricular pressure, as for example during anesthesia or critical care monitoring, the invention also presents methods for real time calculation of the left ventricular fiber stress, for accurate observation of the physiological function of the myocardium. The invention hence devices the use of such imaging for monitoring of cardiac performance, for example during anaesthesia or other critical care monitoring.

The invention further presents detailed designs of ultrasound transducer arrays that allows sector scanning of an ultrasound beam in three or four 2D scan planes that are rotated around a common axis. The design is composed of at least two active piezoelectric, phased array transducer layers mounted face to face in a sandwich structure that is mounted on a backing material. The piezoelectric sandwich front face is connected to the load material through a set of elastic impedance interfacing layers for improving the acoustic power coupling between the piezoelectric layers and the load material. In a special wide band design, the impedance interfacing layer closest to the piezoelectric layers has the same characteristic impedance as the piezoelectric layers, as described in [5].

Both the front and back side electrodes of each array layer are formed as a set of isolated, parallel finger/element electrodes that are connected to a switching circuit. The finger/element directions on the front and back side of each layer form angles to each other. The finger/element directions of the different piezoelectric layers are arranged so that the finger directions of at least one set of electrodes of one layer form an angle to the finger directions of at least one set of electrodes of other layers.

The switching circuit is electronically controlled so that the full set of finger electrodes of each piezoelectric layer surface can selectively be connected either to the hot wires of a phased array ultrasound imaging instrument, or connected to signal ground. This allows electronic selection of one of a set of 2D scan plane directions for each transmitted pulse. With limited number of beams in each 2D image, one can get so high frame rate that when switching the scan planes sequentially, the images in the different scan planes show practically real time display of the object. Hence, the imaging instrument can show real time display of 3 or 4 scan plane directions, for example to observe regional contraction abnormalities of the myocardium.

Transmitting a wide beam and covering it with several narrow receive beams in parallel, one can increase the frame rate by a factor of order 2-6. Other increase in the frame rate is obtained by reducing the beam density where the scan planes intersect, and where the beams have limited information about the object, for example internal in the left ventricle while the ventricular walls are covered with high density of beams for ventricular wall motion analysis. For special high frame rate observation of the heart in the different scan planes, one can keep the same scan plane direction for a whole cardiac cycle, and change direction of the scan plane right before the onset of the myocardial contraction, for example triggered by the ECG signal from the heart.

The invention also shows a special embodiment where the multi-scan plane phased array is mounted at the tip of an endoscope for imaging of objects from internal in the body. In particular, such a method is useful for transesophageal imaging of the heart in many scan planes, for example to assist anesthesia monitoring during surgery. The transesophageal array can further be rotated mechanically in the endoscope for detailed alignment of the scan planes with interesting areas, or to increase the number of scan planes that are imaged.

Ultrasound contrast agents can be used to observe regional variations of myocardial blood perfusion. Such contrast agent can also be administered for efficient determination of the ventricular volumes. An example of an array embodiment is given that allows imaging in multiple frequency bands. This embodiment is well adapted for transmission of ultrasound pulses within one band of frequencies, and reception in sub, $2^{nd}$, $3^{rd}$, or $4^{th}$ harmonic component of the transmit band. Such harmonic imaging is especially useful for the detection of ultrasound contrast agent, both to assess regional variations in the myocardial blood perfusion, and for automatic detection of the volume of ventricular cavities, and for detection of regions of tumors with increased vascularization.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIG. 1 shows in FIG. 1a an example of an imaging system that allows real time imaging of an object simultaneously in three 2D scan planes, while

FIG. 3 shows a two-layer array with finger electrode structure that allows for electronic selection of three 2D scan planes as in FIG. 1a;

FIG. 10 shows by example displays of the image data, where

DETAILED DESCRIPTION OF THE PRESENTLY PREFERRED EMBODIMENTS

Several example embodiments according to the invention is presented in the following. It is clear that this presentation is meant for illustration purposes only, and by no means represents limitations of the invention, which in its broadest aspect is defined by the claims appended hereto.

Figure 1A:
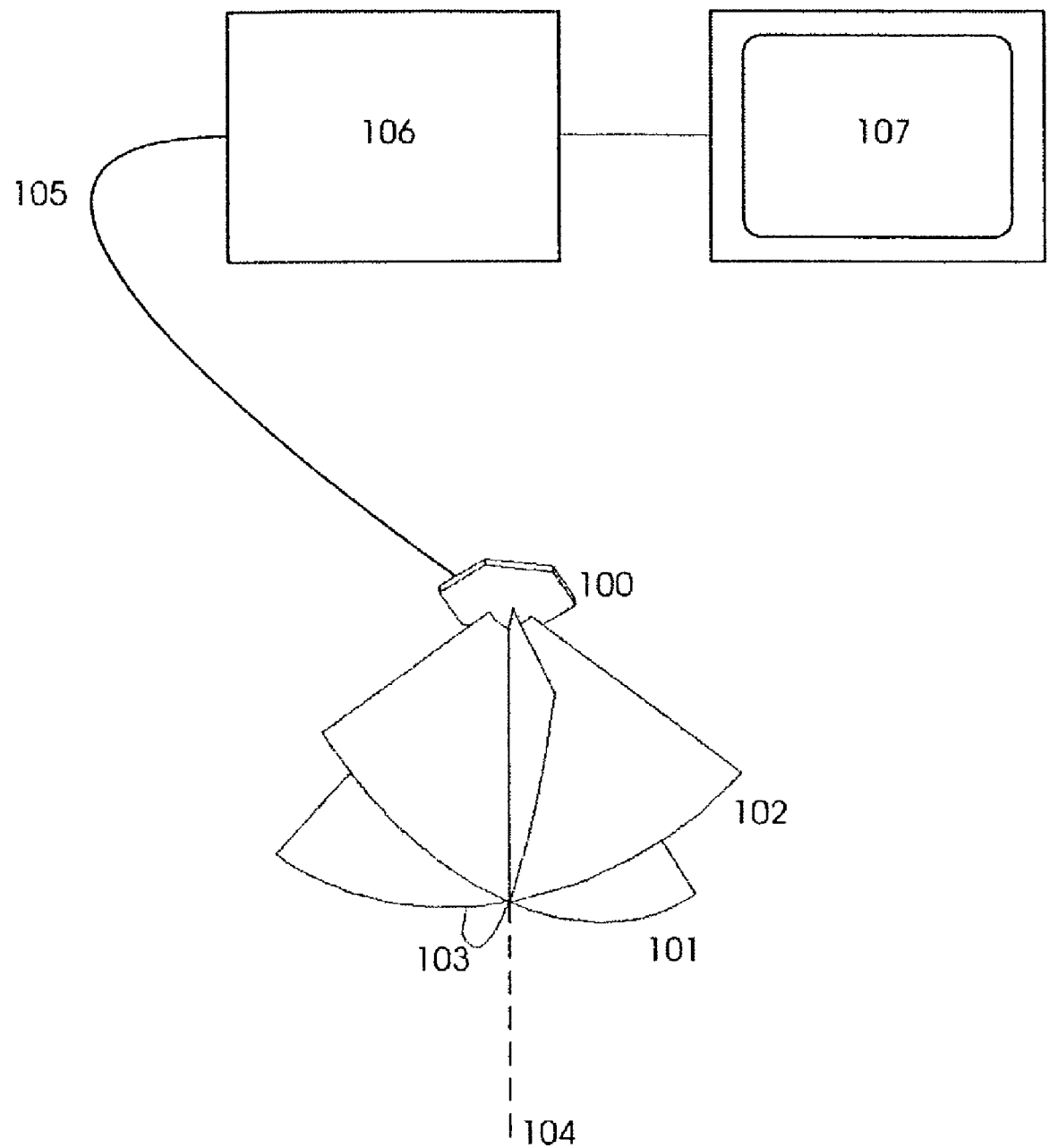

As an example embodiment of the invention, FIG. 1a shows a transducer array 100 that is capable of transmitting pulsed ultrasound beams with directions freely and electronically steerable within for example three 2D sector scan planes 101, 102, and 103, that are rotated with different angular directions around a common axis 104. The transducer array is connected via a cable 105 to an ultrasound imaging instrument 106 with image outputs given to a display screen 107.

In a typical imaging situation, the ultrasound imaging instrument 106 directs signals to the transducer that transmit ultrasound beams in selected directions within the 2D scan planes 101-103. The back scattered signal is for each beam direction analyzed in the instrument to generate a set of image parameters for a set of range samples along the beam directions. Typical image parameters can be a compressed version of the backscattered amplitude for imaging of tissue structures, or Doppler frequency parameters for imaging of blood velocities, velocities of tissue movement, or strain of tissue regions, for example myocardial strain, or enforced strain on a tumor for elastography imaging, all according to known methods.

The beam scanning can be done in many ways, for example sequentially for each 2D scan plane in turn, or in a spiral pattern as described below. The image parameters for the beam directions that belong to each scan plane are then grouped together to form 2D images of the image parameters for the scan planes. These 2D images are then shown in real time on a display screen, for example as the images 111, 112, 113 in FIG. 1b. This Figure also illustrates a time trace 114 of a cardiac ECG to be used as timing reference, with an area 115 for display of alphanumeric data extracted from the images or other measurements.

With 64 beams per 2D image with an image range of 15 cm, one typically obtains 72 2D images per second. With 3 sequential 2D scan planes one hence gets 24 full updates of the three 2D scan-planes per second. Increasing to 4 sequential scan planes, one gets 18 full updates per second of the four 2D scan-planes. 64 beams with a 16 mm aperture array at 3 MHz give a total opening angle of the 2D image around ~60 deg with full angular sampling of the 2D image.

Transmitting a wide transmit beam and covering it with several (for example 2-6) narrow receive beams in parallel, allows an increase of the image rate by a factor 2-6. This also gives time for expanding the scan angle of each 2D scan-plane, for example to 90 deg. The image rate and/or the width of the 2D scan can also be increased by reduced beam density, especially in the overlap region of the planes close to the axis 104, and in regions with little information about the object, like the middle of the ventricle with apical long axis imaging of the heart. If faster 2D image rate is needed, for example to study details in the onset of cardiac contraction and relaxation, one can image a full cardiac cycle for each scan plane, and change the scan plane at the end of the cardiac cycle, for example triggered by the ECG signal.

For assessment of regional wall motion abnormalities of the heart, it is important that the time delay is minimal between the beams that samples the wall in different regions. A useful cardiac scanning is then obtained by apical imaging of the ventricle, locating the array center axis 104 along the left ventricle long axis, which in FIG. 1c is shown as normal to the Figure in the center. A typical myocardium cross section is shown as the area 125 in this image. Cross sections of the scan planes 101, 102, 103 are shown as 121, 122, 123. In this particular beam scanning pattern, the scan plane direction is switched in a circle for each sequential beam direction, so that the beam scanning occurs in a spiral cone with steadily increasing/decreasing angle of the beam to the axis 104. The crosses indicates some of the interrogating beams, where a selection 126, 127, 128, indicate a subset of the beams that follow each other in a sequence in the direction 129. At the last beam 130 with this beam angle to the axis 104, the beam angle is increased so that the next beam cross section is 131 in the same scan plane 121 as the beam 126, but with larger (or possibly smaller) beam angle to the center axis 104. The beam direction 130 is in this example followed by the beam direction 132 in 2D scan plane 122 and so on as indicated by the arrows. As the myocardium 125 with this scanning pattern is imaged with beams of close to the same opening angle between the beam and axis 104, one can cover the whole myocardium in a limited time interval. Typically, the myocardium is covered with around 10*6~60 consecutive beams that can be collected in a time interval of 10-15 msecs with a frame rate of ~80 frames per second. This provides a highly adequate volume frame rate to study regional variations in the contraction, relaxation pattern of the myocardium.

Figure 1B:
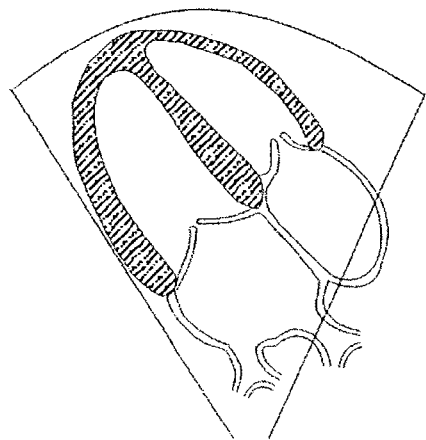
FIG. 1b shows an example display of 3 real time 2D images.
Figure 1B:
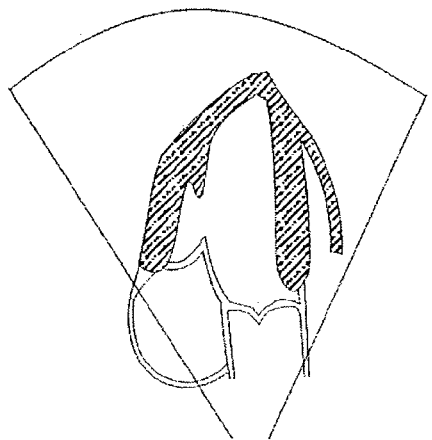
Figure 1B:
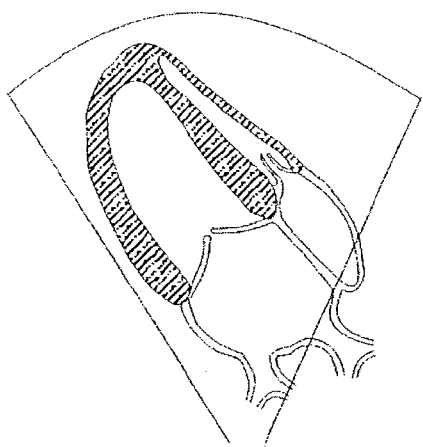
Figure 1B:
Figure 1C:
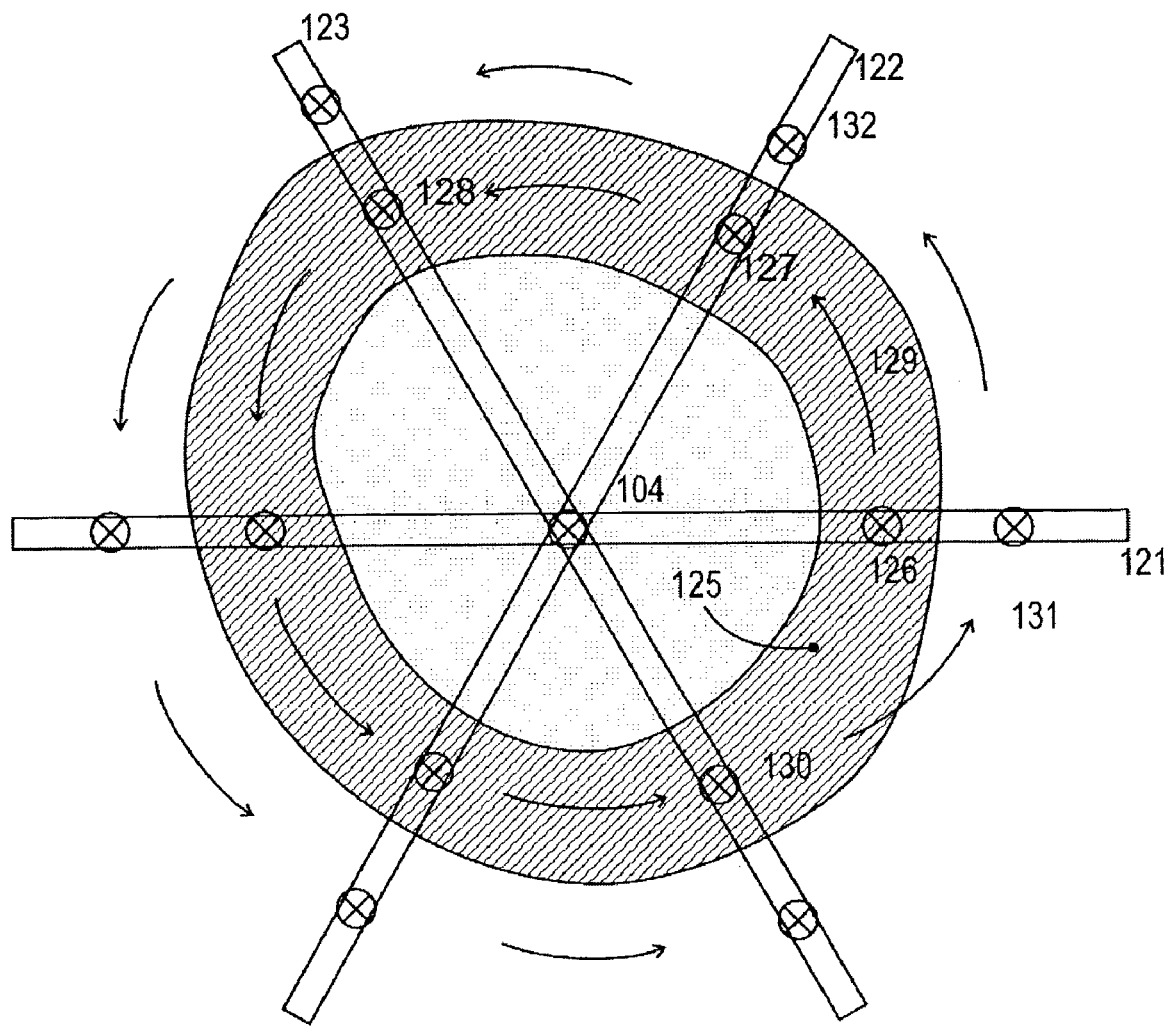
FIG. 1c illustrates a spiral scanning of ultrasound beam for observation of the myocardium with minimal lag between beams across the myocardium.

For display, the image data from the beam directions belonging to each 2D scan plane are grouped together to form 2D images that are displayed in real time as exemplified in FIG. 1b. The multiple scan planes can then be used for real time observation of regional wall motion in the heart and volume calculations of the heart cavities, both for diagnosis and for peri and post surgical monitoring, and monitoring in other critical care situations, as discussed below.

Two embodiments of transducer arrays that provide the beam scanning according to the invention, is now presented.

Figure 2:
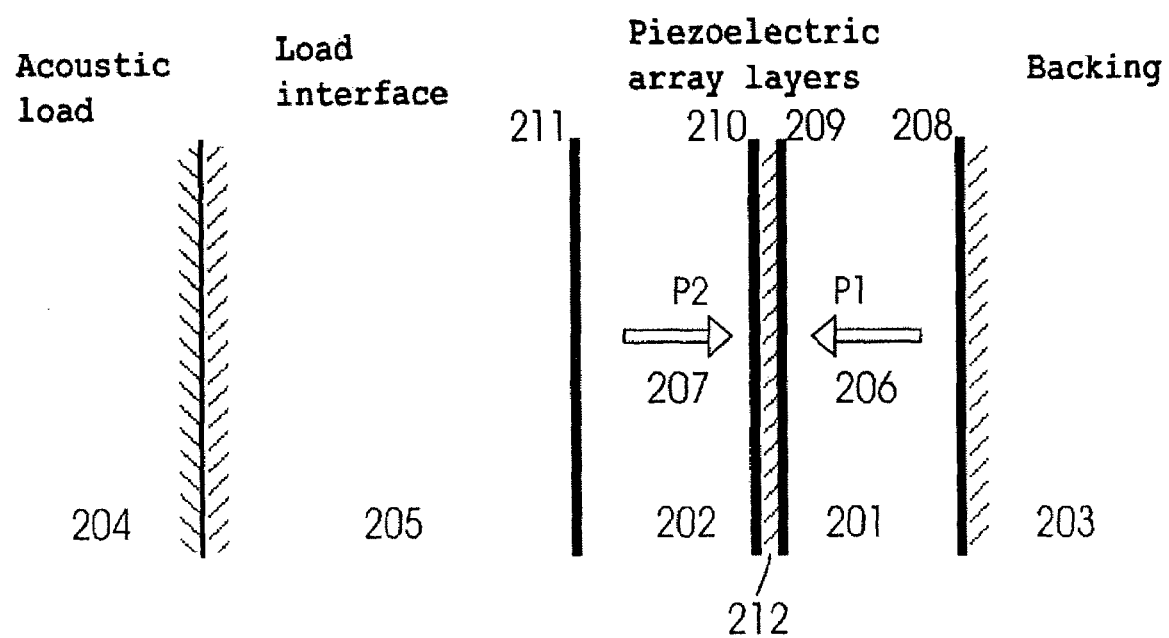
FIG. 2 shows a cross section in the thickness direction of a typical layer structure of the transducer array, according to the invention.

FIG. 2 shows a cross section in the thickness direction of a phased array according to the invention, where 201 and 202 show two piezoelectric array layers mounted on a backing structure 203 with so high acoustic power absorption that reflected waves in the backing material can be neglected. The piezoelectric layers are covered with phased array finger/element electrodes 208, 209, 210, and 211. The front electrodes 209 of the back layer and the back electrodes 210 of the front layer are electrically isolated from each other with the thin layer 212, for example a glue film. Between the piezoelectric layers and the acoustic load material 204, the structure contains a set of elastic layers 205 to interface the characteristic impedance of the piezoelectric layers (201, 202) to that of the load material 204.

A method for such impedance interfacing that gives a particularly wide bandwidth, is given in [5], where the first layer of structure 205 in contact with the piezoelectric layers contains an elastic layer with close to the same characteristic impedance as the piezoelectric layers, followed by layers with falling characteristic impedance towards the load. Such an impedance interfacing is particularly useful when using the two piezoelectric layers in electrical parallel coupling to transmit a low frequency pulse, and then receive higher harmonic components ($2^{nd}$ to $4^{th}$) of this pulse on for example the back layer 201, as described below. One might also transmit a pulse on layer 201 and receive a sub-harmonic pulse on the electrical parallel of layers 201 and 202, as described below. In other situations one can use more narrow-band impedance interfacing layers 205, according to standard methods.

An example of dicing of the piezoelectric plates to obtain a reduced characteristic impedance ceramic/polymer composite, with an arrangement of electrodes that allows phased steering of an ultrasound beam in three 2D planes, is shown in FIG. 3, which shows the piezolectric layers and electrodes from the faces. In FIG. 3a, 301 shows dicing grooves of the ceramic piezoelectric layers, the same for both layers, with the remaining ceramic posts/islands as 302. The dicing grooves 301 are filled with polymer to produce a ceramic/polymer composite structure with characteristic impedance reduced from that of the bulk ceramic material by a factor around 0.5, depending on the relative volume fill of ceramic.

Figure 3A:
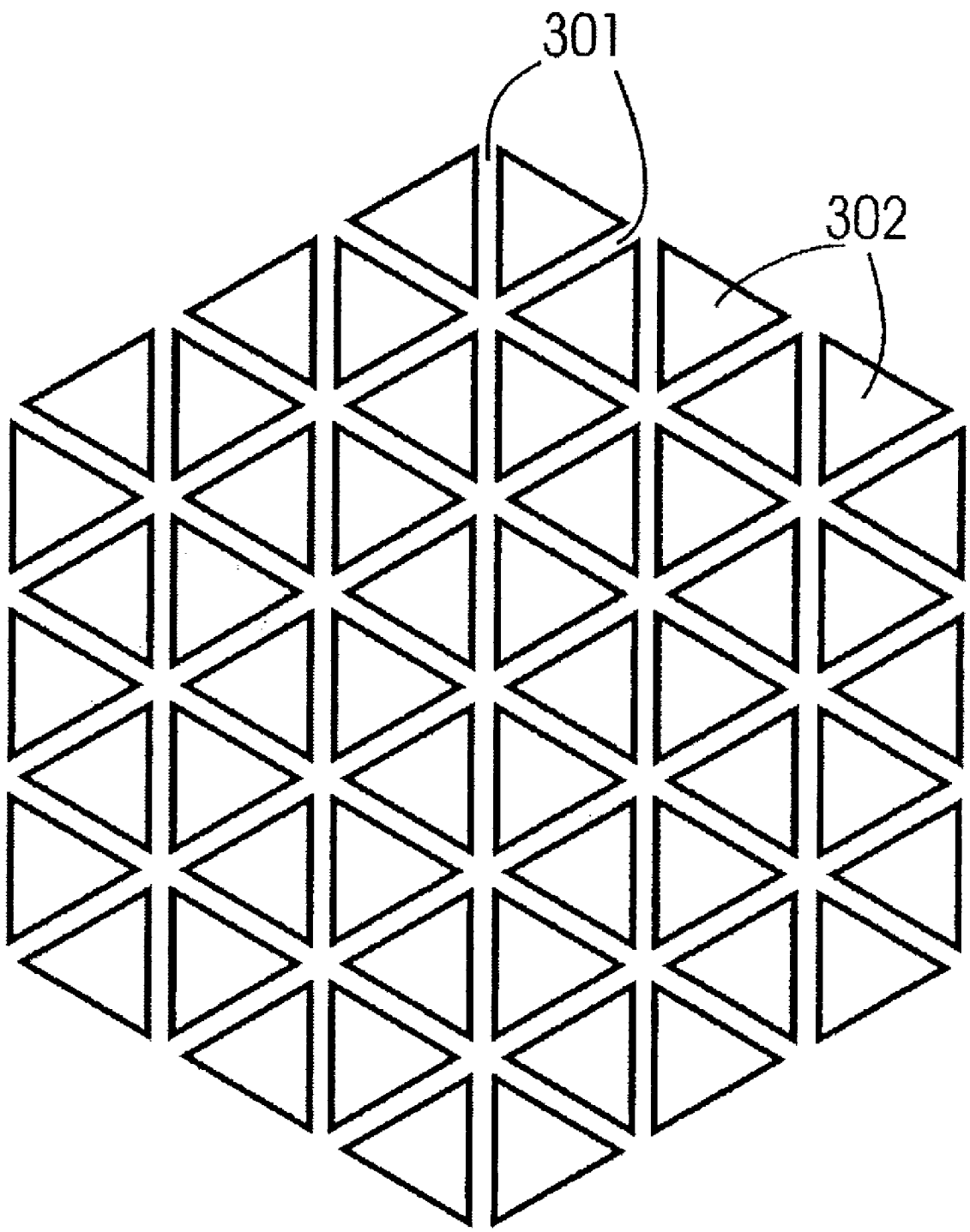
Figure 3B:
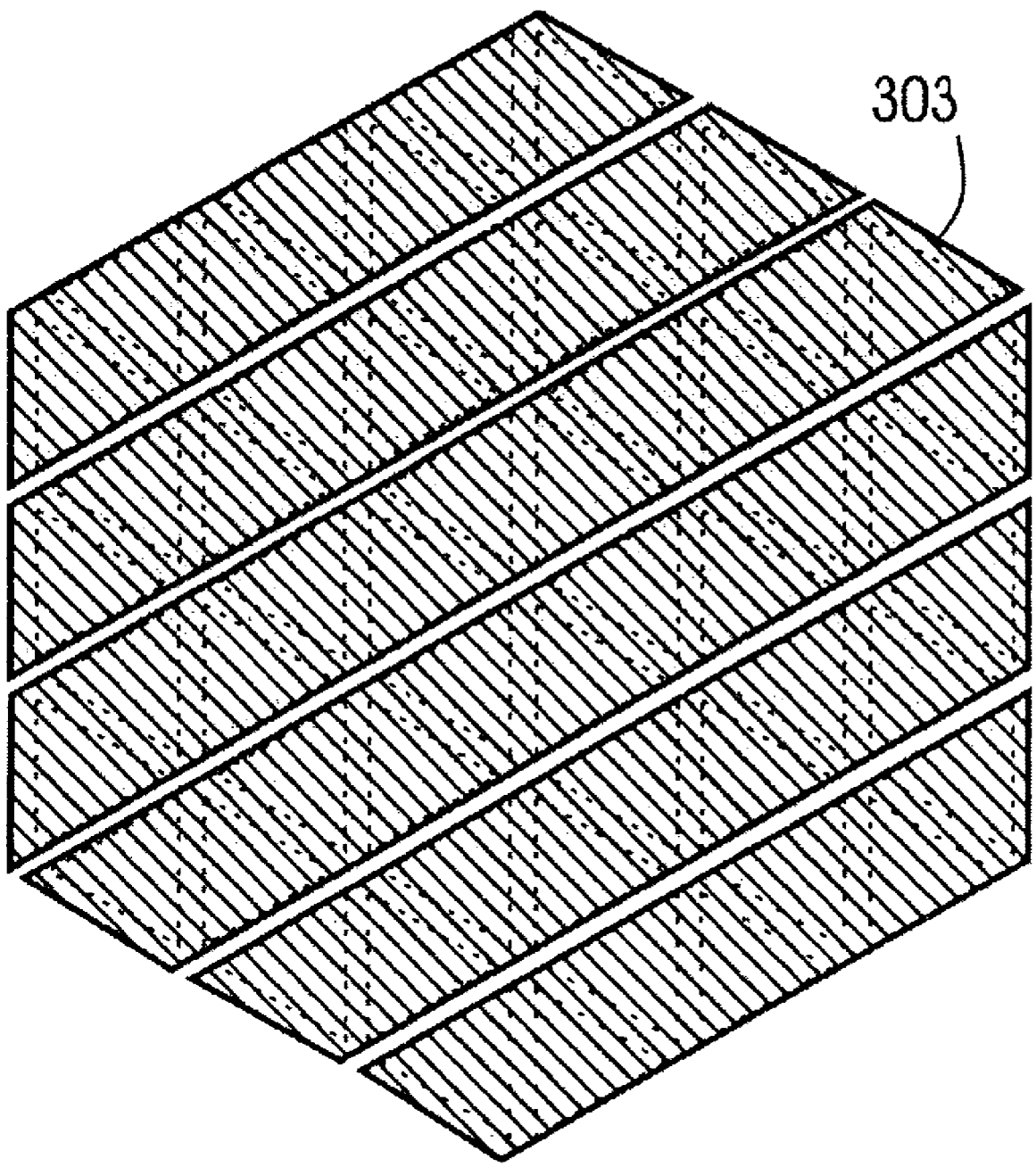
Figure 3C:
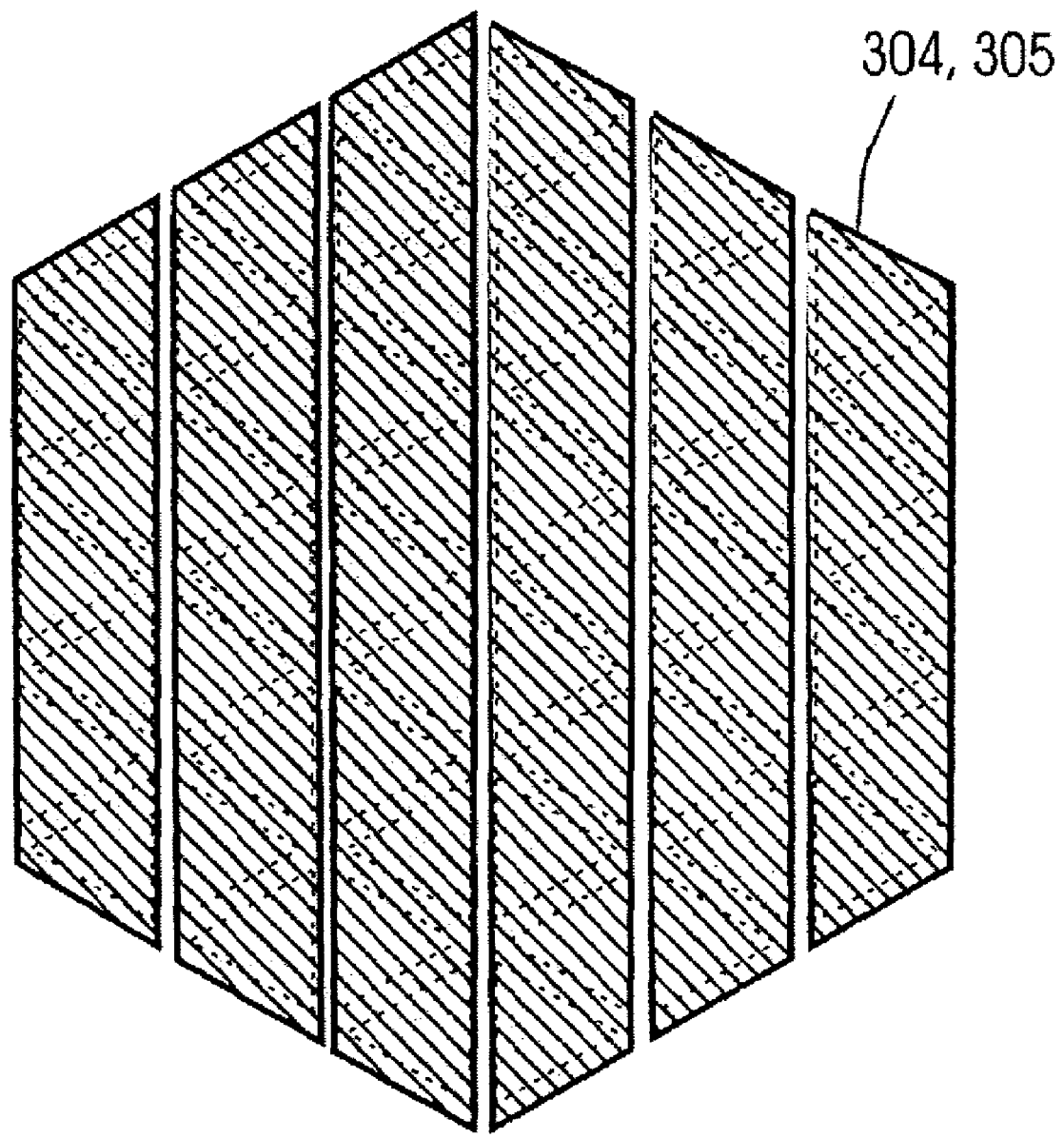
Figure 3D:
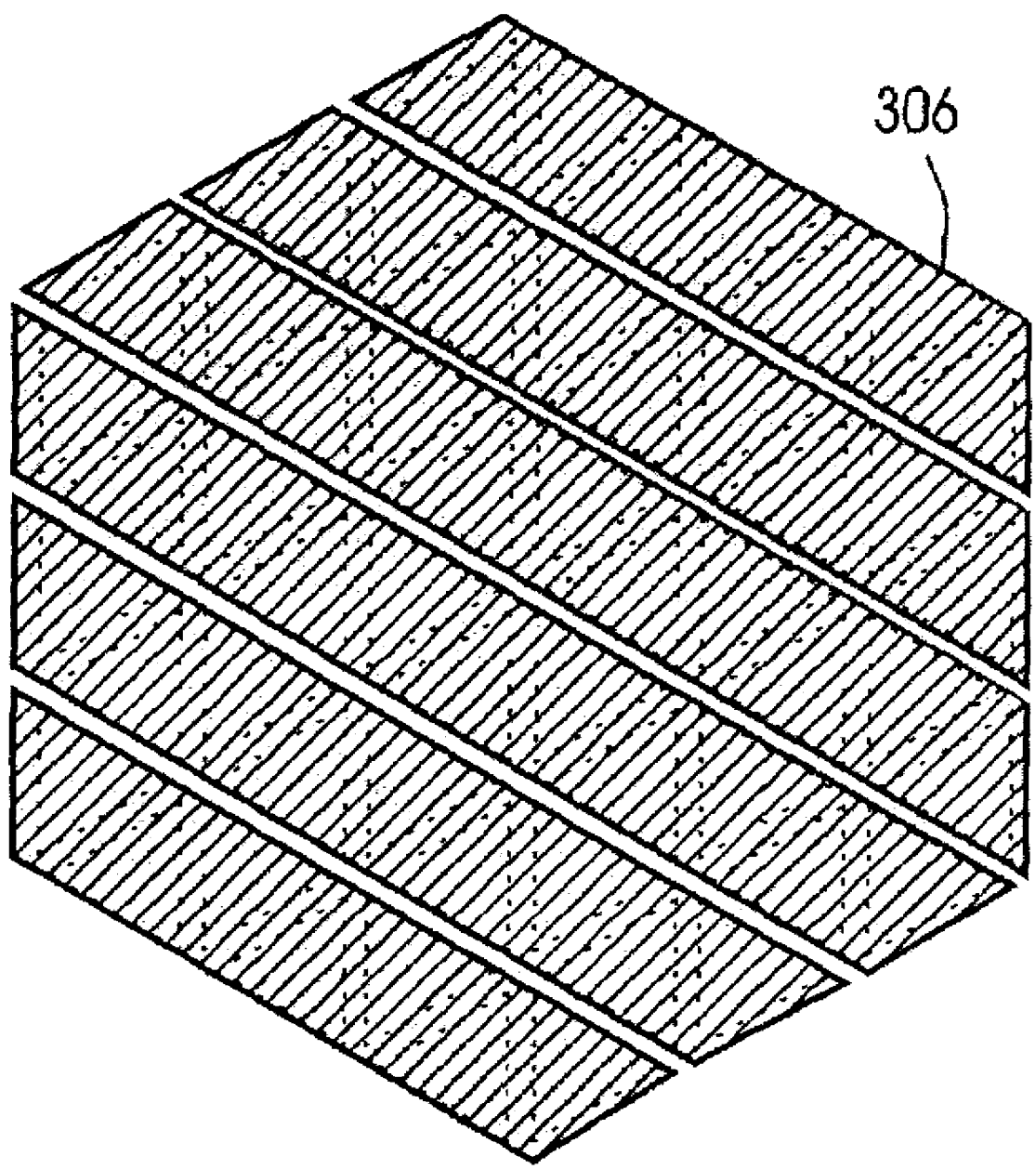

In a particular embodiment according to the invention, the back face of the piezoelectric layer 201 is covered with a set of divided finger/element electrodes 303 as shown in FIG. 3b, while the front face of the back layer 201 and the back face of the front layer 202 are covered with divided finger electrodes 304 and 305 that have the same shape and direction, as shown in FIG. 3c. The front face of piezoelectric layer 202 is covered with divided finger electrodes 306 shown in FIG. 3d. The electrode sets 303-306 corresponds to the electrodes 208-211 in FIG. 2, where the finger electrodes 304 and 305 are electrically isolated from each other by the layer 212 as illustrated in FIG. 2.

A principle drawing of the 2D scan planes that can be obtained with the array in FIG. 3, is shown in FIG. 1a, where the array is illustrated as 100. Grounding electrode sets 304/209, 305/210, and 306/211, and operating the back electrodes 303/208 as the hot electrodes of the elements of a linear phased array transducer, one will obtain a 2D image scan plane shown as 101 in FIG. 1a. Grounding electrode sets 303/208, 305/210, and 306/211, and operating the electrodes 304/209 as the hot element electrodes of a phased array, one obtains a 2D image scan plane shown as 102 in FIG. 1a. Grounding electrode sets 303/208, 304/209, and 305/210, and operating the front electrodes 306/211 as the hot element electrodes of a phased array, one obtains a 2D image scan plane shown as 103 in FIG. 1a.

Choosing the dicing and electrode directions at 60 deg angle to each other as shown in FIGS. 2a-2d, one gets an equilateral triangle of the ceramic islands, and 60 degrees angle between the 2D scan planes in FIG. 1a, which gives an even angular sampling of the object. With such angles, one gets equal dimensions of the ceramic islands of the composite allowing equal width of the electrodes/elements of the array. Other angular divisions of the array/electrodes is also possible, for example to sample the left ventricle closer to other, wanted image planes.

Figure 4:
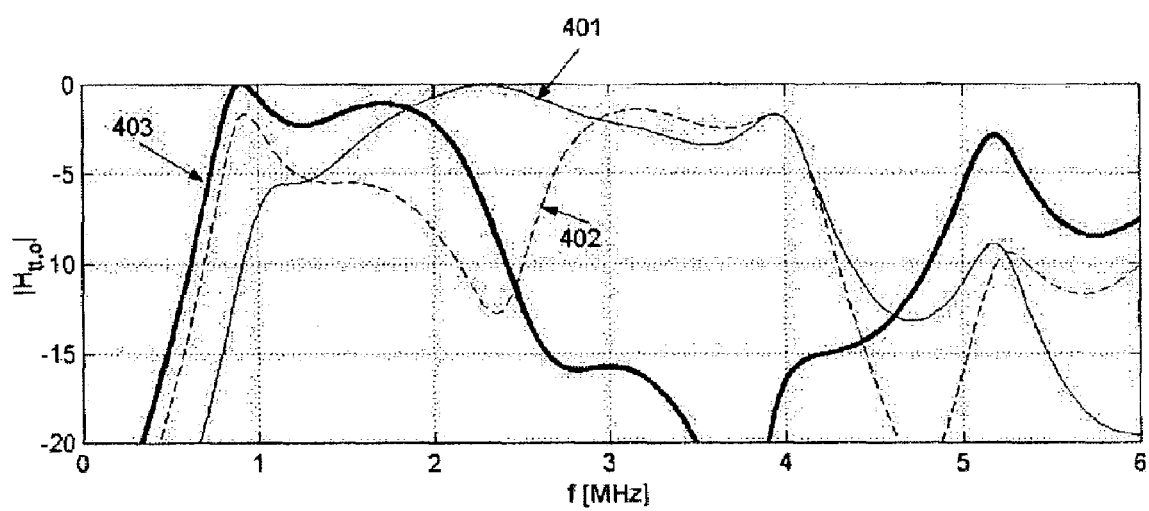
FIG. 4 shows transmit transfer functions that can be obtained with the transducer structure in FIG. 3.
Figure 5A:
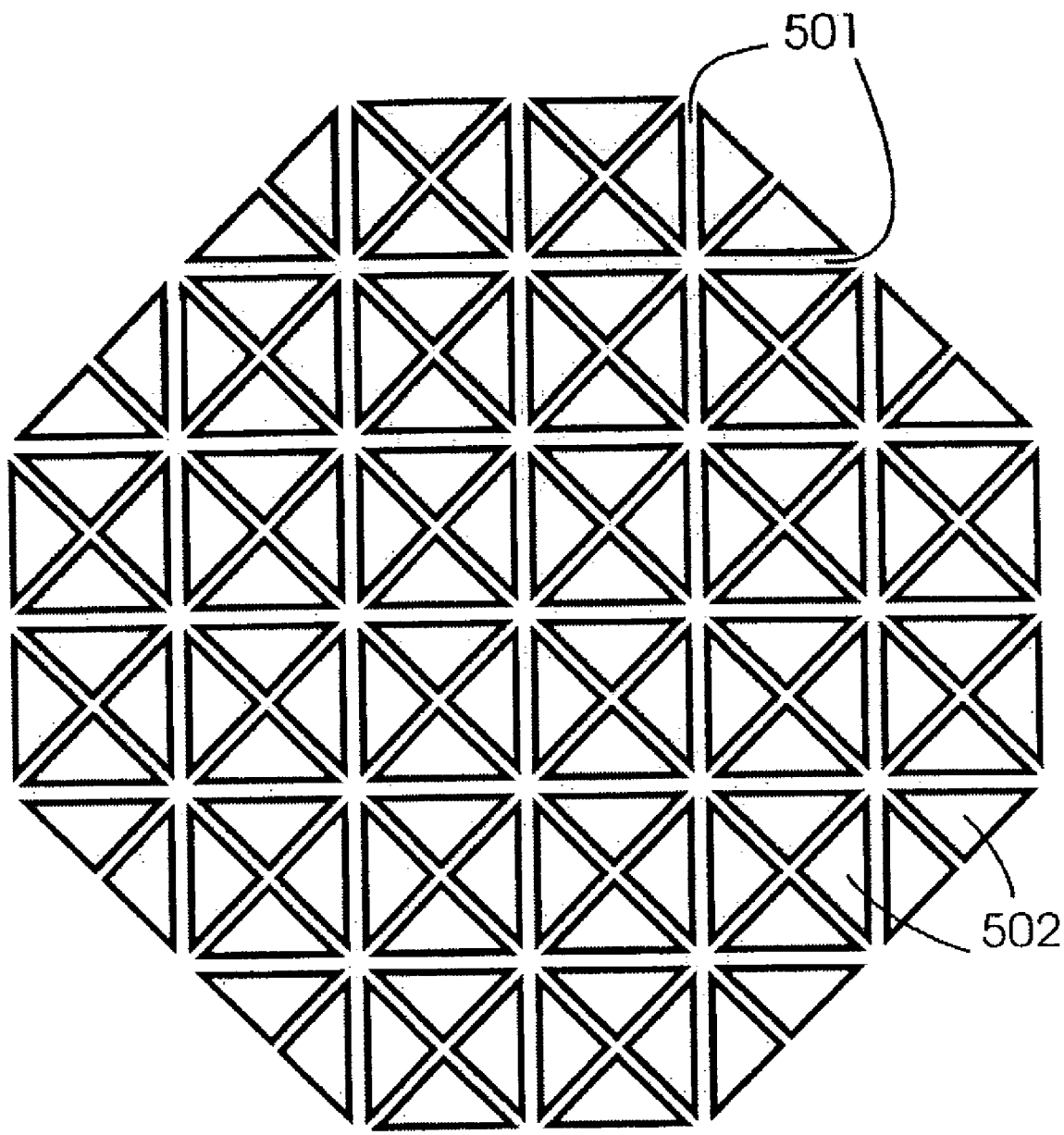
FIG. 5 shows yet another transducer array structure with two piezoelectric layers according to the invention that allows for electronic selection of 4 scan planes.
Figure 5B:
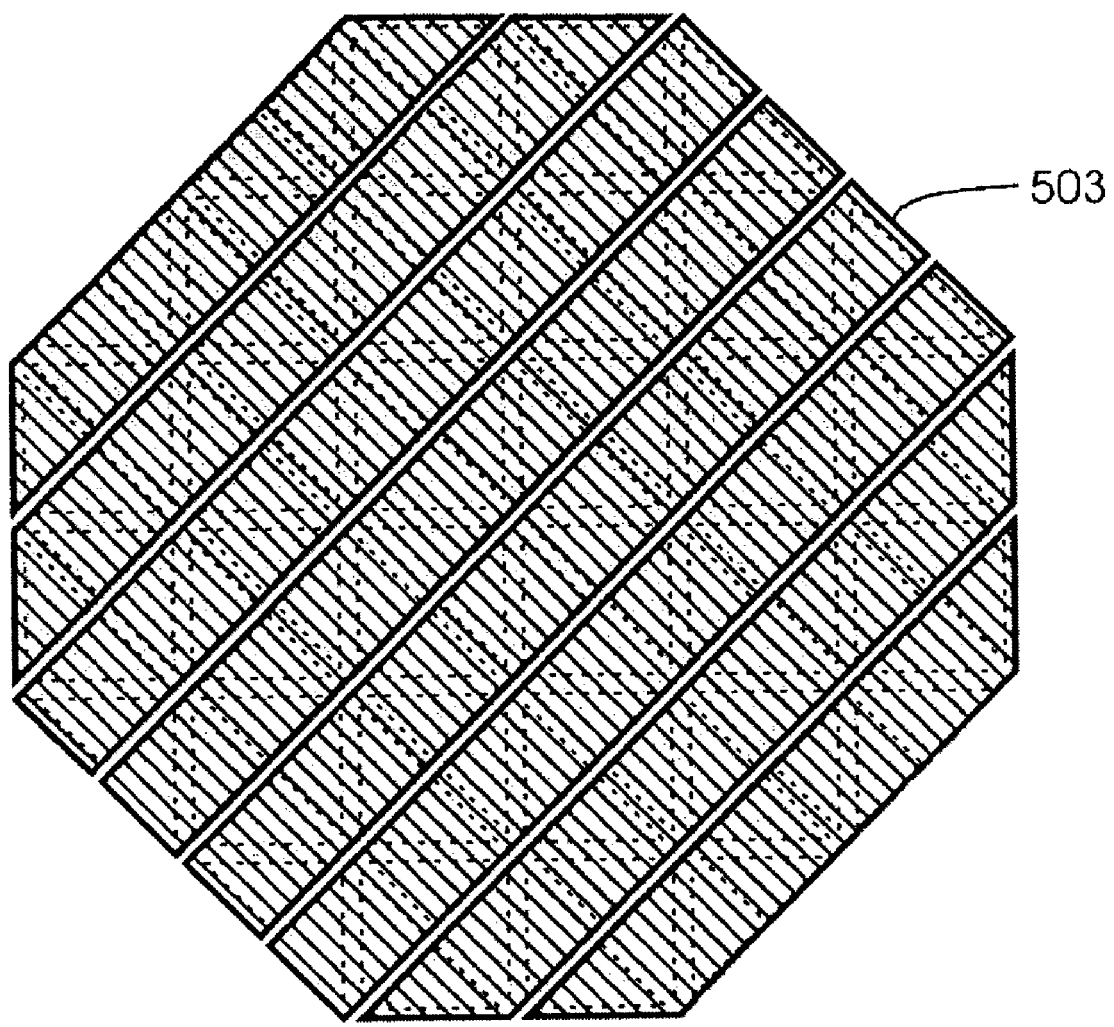
Figure 5C:
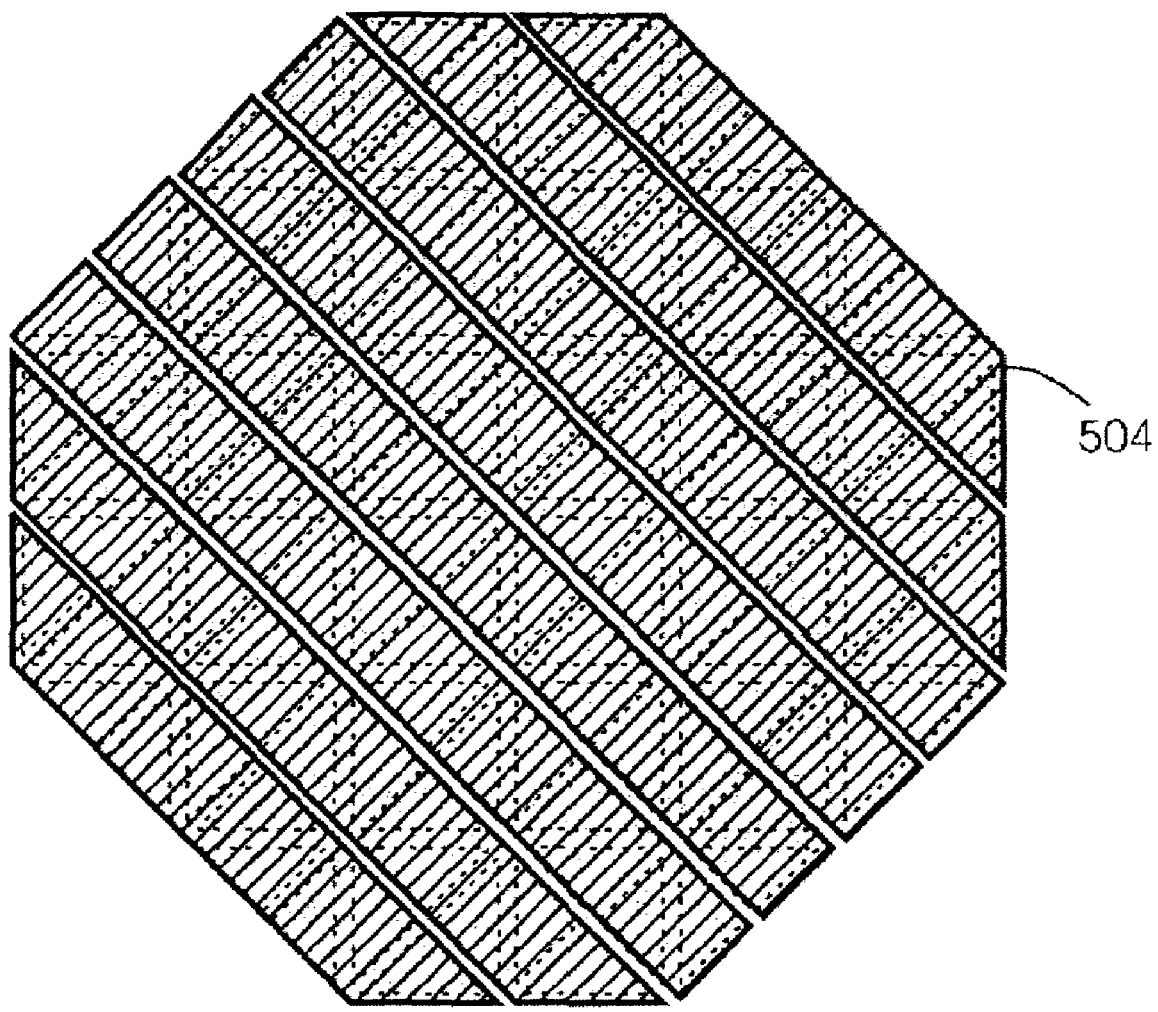
Figure 5D:
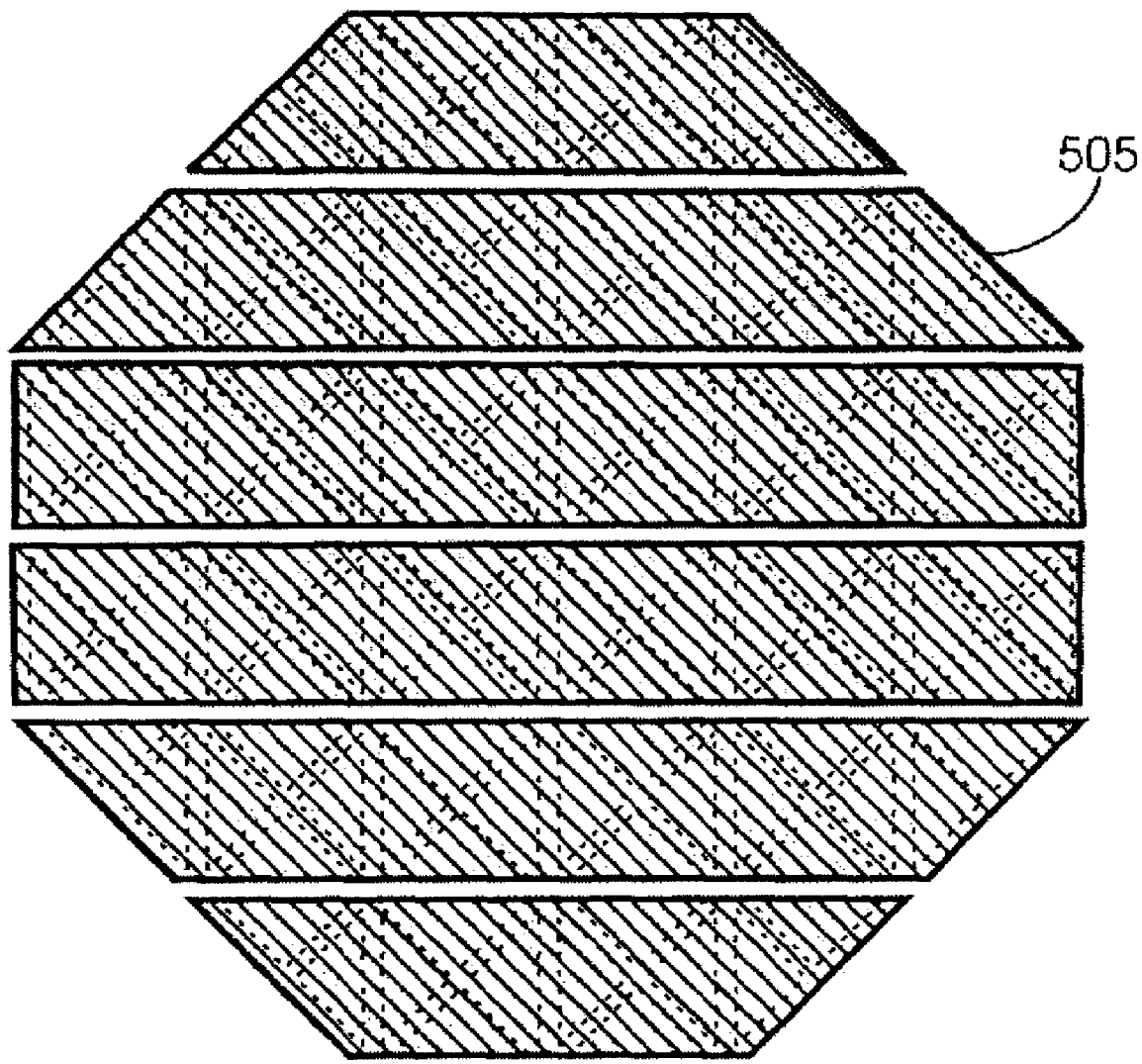
Figure 5E:
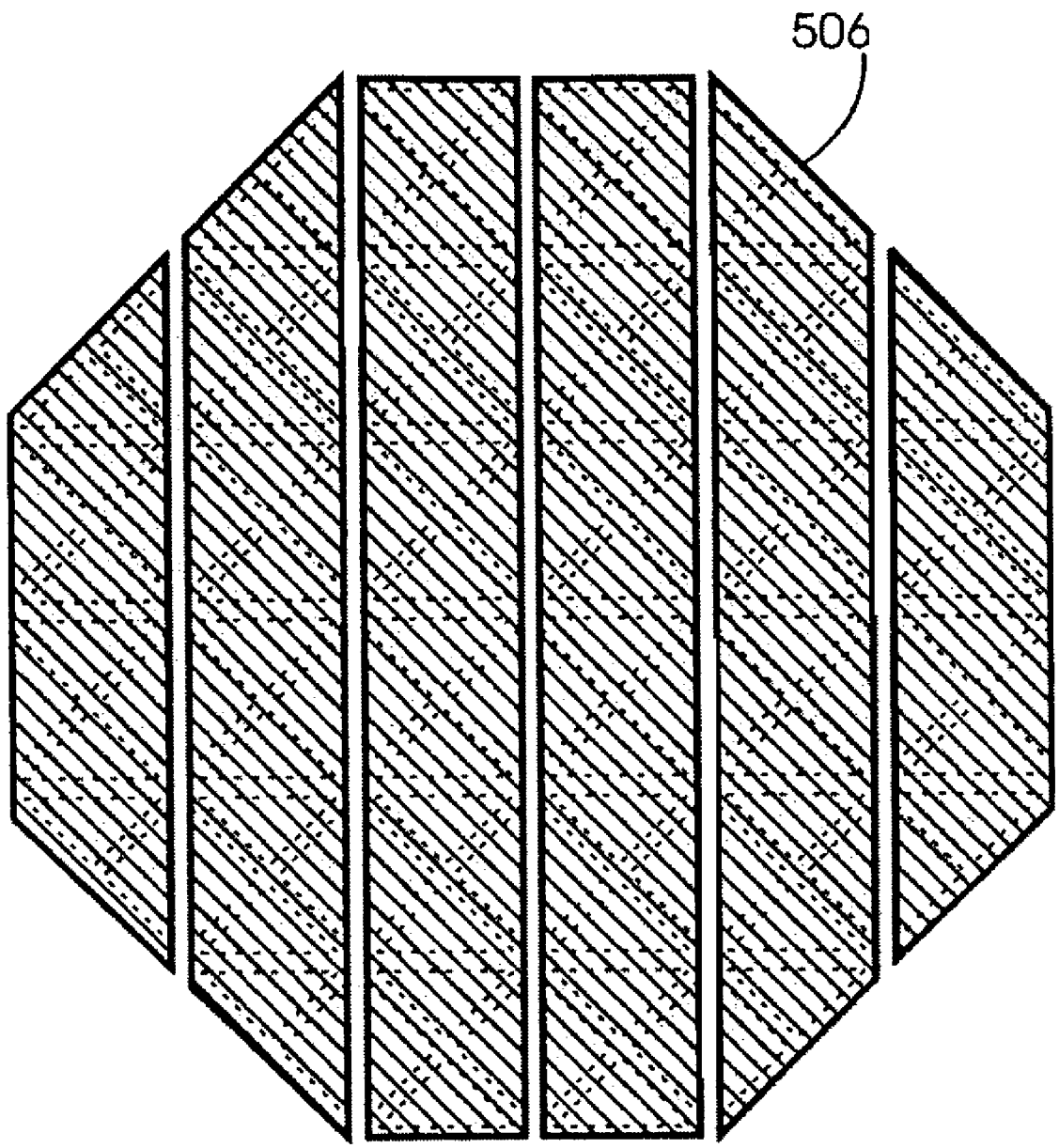

The transduction capabilities of the array are conveniently described by the transmit transfer functions $H_{ti}(\omega)$ of the array elements, defined as the transfer function from the transmit voltage on the electrodes to the vibration velocity on the element front surface. Typical transmit transfer functions for the back layer 201 and the front layer 202, with the other layer electrically shorted, are shown as 401 and 402 in FIG. 4, respectively. Both scan planes 101 and 102 in FIG. 1a are using the back piezoelectric layer 201 of FIG. 2 with the transfer function 401 with close to flat response in a wide frequency range of 1.5-4.2 MHz. Scan plane 103 of FIG. 1a is using the front piezoelectric layer 202 of FIG. 2 with the transfer function 402 of FIG. 4. We see that both layers have similar transfer function (401 and 402) in the 2.8-4.2 MHz frequency range. Hence, within this frequency band, the pulses for the third scan plane 103 obtained with the front layer can be made similar to the pulses for the scan planes 101 and 102 obtained with the back layer.

In FIG. 2, the polarizations of the piezoelectric layers are shown as P1 (206) and P2 (207). With opposite directions of the polarizations as shown in this example, one obtains electrical parallel coupling of the layers by grounding the front (211/306) and back (208/303) electrodes and operating the mid electrodes (209/304 and 210/305) as the hot electrodes of a phased array. The transmit transfer function for such electrical parallel coupled operation of the piezoelectric layers, is shown as 403 in FIG. 4. We notice that this transfer function covers a lower band of frequencies from 0.8-2.2 MHz.

Hence, aside from the ability to electronically select three scan planes, the structure allows for operations in multiple frequency bands in scan plane 102, both for regular $1^{st}$ harmonic imaging in multiple frequency bands and for harmonic imaging. For example, with electric parallel coupling of the layers as described above, one can transmit in a low frequency band 403. Grounding electrodes 208/303, 210/305, and 211/306 while operating 209/304 as the hot element electrodes of a phased array, one can receive $2^{nd}$, $3^{rd}$, or $4^{th}$ harmonic components of the transmit band 401 with the back layer. Similarly, one can transmit in a high frequency band with grounded electrodes 208/303, 210/305, 211/306 and operating electrodes 209/304 as the hot element electrodes of a phased array, and receive sub harmonics of the transmit band by grounding electrodes 2081303 and 211/306, and connecting electrodes 209/304 and 210/305 to operate the two layers electrically in parallel for a low frequency band.

A dual piezoelectric layer structure that provides free selection of 4 scan planes, is shown in FIG. 5, which shows the piezoelectric layers and electrodes from the faces as in FIG. 3. In the thickness direction, the structure contains two piezoelectric layers, with an impedance interface of elastic layers to the load, as shown in FIG. 2. In FIG. 5a is shown an example of dicing of the ceramic piezoelectric layers, where 501 shows the shows the dicing grooves and 502 shows the ceramic posts/island. The difference to the structure in FIG. 3 is found in the ceramic dicing to form the ceramic/polymer composite, and the directions of the finger/element electrodes. In particular, for the structure in FIG. 5 the two sets of intermediate electrodes 504/209 and 505/210 between layers 201 and 202 have different directions as shown in FIGS. 5c and 5d. The back side of layer 201 is furnished with a set of finger electrodes 503/208 shown in FIG. 5b, and the front side of layer 202 is furnished with a set of finger electrodes 5061211 shown in FIG. 5e.

Figure 6:
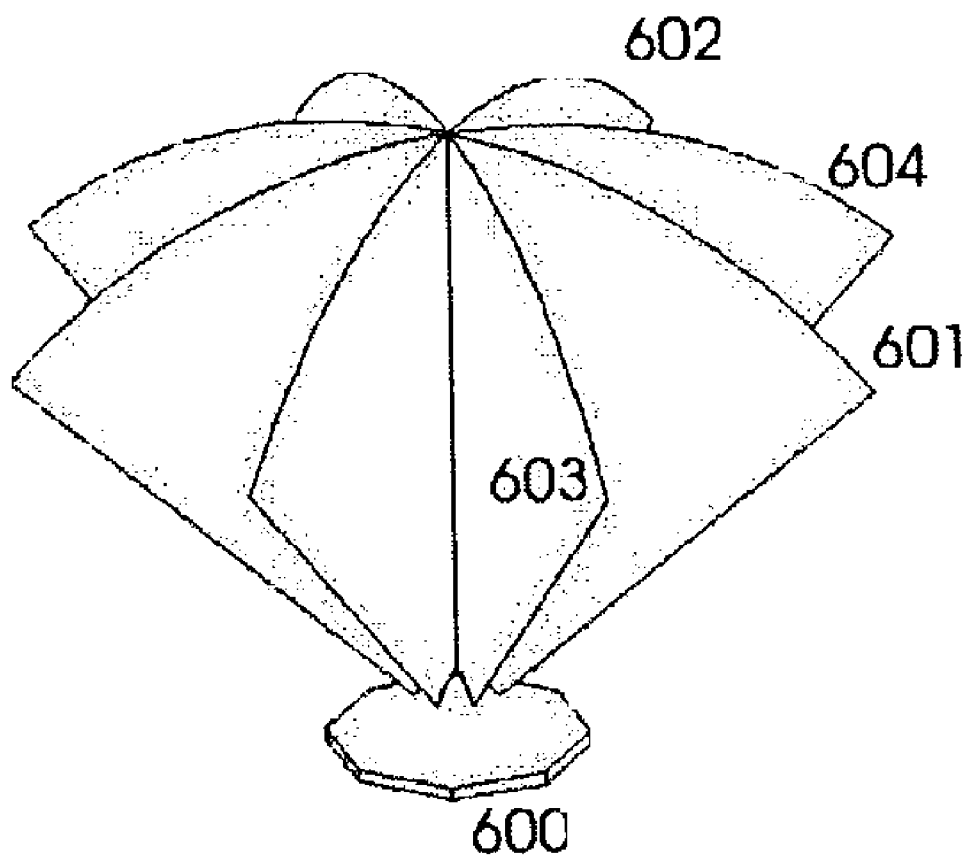
FIG. 6 shows example scan planes that can be selected with the transducer array structure in FIG. 5.

We see that by grounding the electrodes 504/209, 505/210 and 506/211, and operating the back electrodes 503/208 as the hot element electrodes of a linear phased array, we obtain a 2D scan plane shown as 601 in FIG. 6. Grounding the electrodes 503/208, 505/210 and 506/211, and operating the electrodes 504/209 as the hot element electrodes of the phased array, we get the 2D scan plane 602 in FIG. 6. Grounding the electrodes 503/208, 504/209 and 505/210, and operating the electrodes 5061211 as the hot element electrodes of the phased array, we get the 2D scan plane 603 in FIG. 6. Grounding the electrodes 506/211, 503/208 and 504/209, and operating the electrodes 505/210 as the hot electrodes of a phased array, we get the 2D scan plane 604 in FIG. 6. The transfer function for the back and the front layers will be the same as 401 and 402 shown in FIG. 4, while this structure will not allow phased array scanning with electric parallel coupling of the layers in the low frequency band 403.

Figure 7:
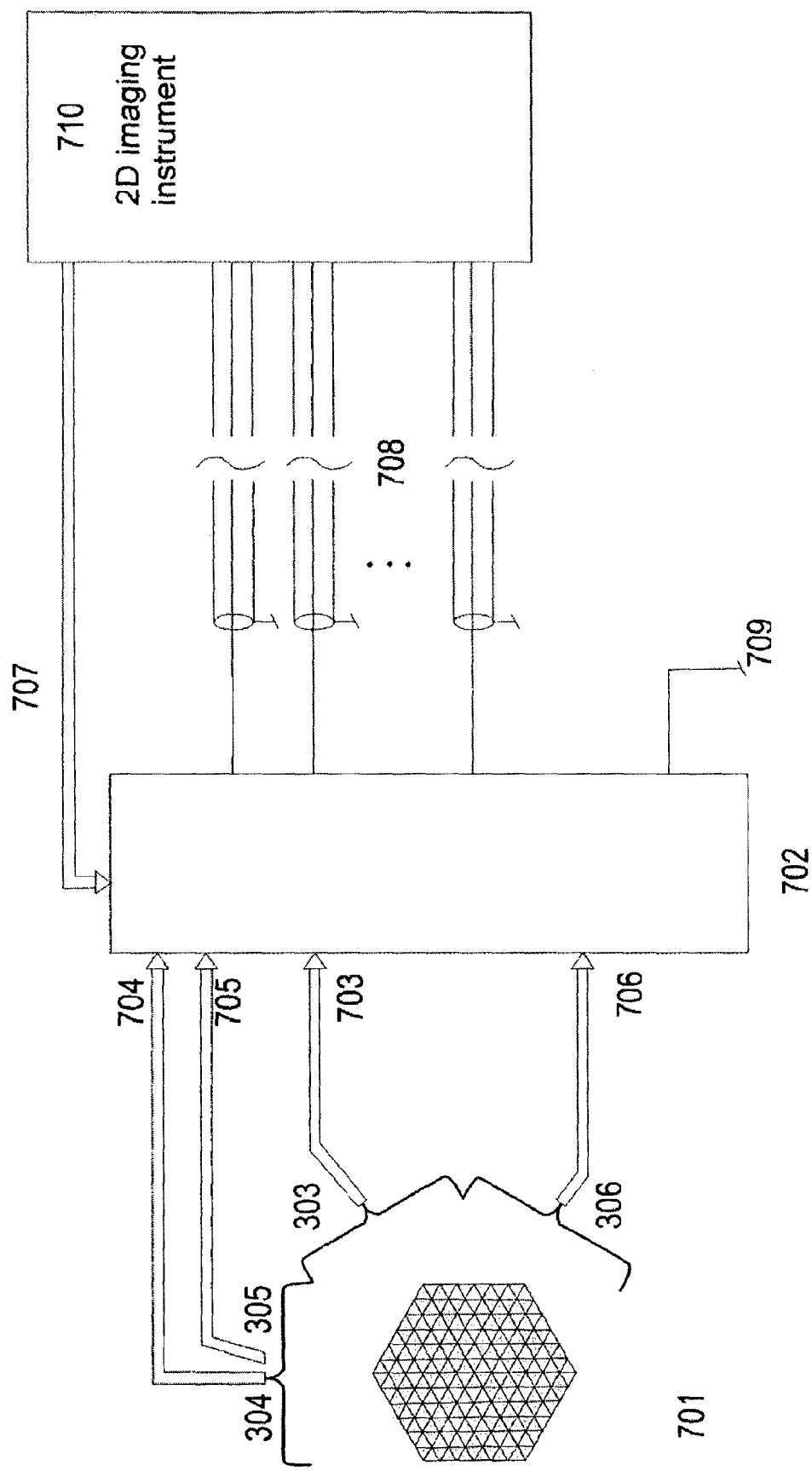
FIG. 7 shows how the scan planes can be selected with an electronic switching circuit located in the ultrasound probe close to the array, to minimize the number of cables connecting the probe to the imaging instrument.

Electronic selection of the illustrated scan planes can be done with an integrated circuit as for example illustrated in FIG. 7. This Figure shows by example as 701 the multi layer/multi electrode transducer array of FIG. 3. Wire sets 703, 704, 705, and 706 connects the electrode sets 303, 304, 305, and 306 to the electronic switching circuit 702, which by the control signals 707 selects the set of electrodes to be connected to the hot wires of the set of coaxial cables 708 that are fed to the imaging instrument 710, and the set of electrodes that are connected to the signal ground level 709. Such an electronic circuit can be mounted close to the array, so that only the cables 708 and the control signals 707 for the scan plane selection is connecting to the imaging instrument.

The transducer array and the scan plane selection circuit is then typically mounted at the tip of a hand held probe for imaging from the body surface, or at the tip of an endoscope, like a gastroscope, for imaging of objects from inside the body, for example transesophageal imaging of the heart or endoscopic imaging of a tumor.

Figure 8:
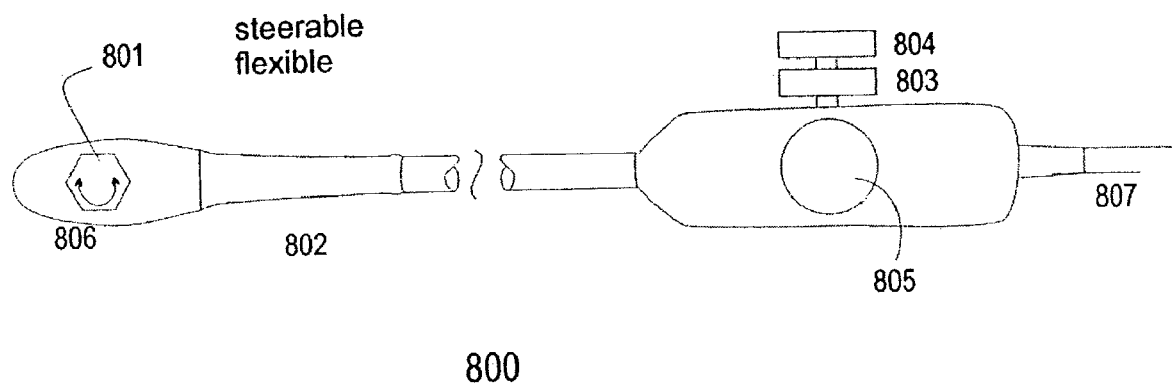
FIG. 8 shows a transesophageal probe with an ultrasound array and electronic switching circuit mounted at a tip of a gastroscope according to the invention.

FIG. 8 shows by way of example a transesophageal probe 800 with an array 801 according to this invention mounted at the tip of the gastroscope that is inserted into the body. The angular directions of the steerable tip 802 of the probe are controlled via wires by the rotation handles 803 and 804, according to standard methods for wire control of the tip of endoscopes. This particular embodiment contains an additional control 805 for rotation as indicated by the arrow 806 of the array 801 within the gastroscope tip 802, for example to adjust one of the scan planes to follow the long axis of the heart. The other scan planes are then grouped around this long axis according to the design of the array. This adjustment can be used for standardized observation of regional wall motion of the heart or accurate calculation of the volume of heart cavities or other objects like tumors. The endoscope probe is connected to the imaging instrument through the cable 807.

Figure 9:
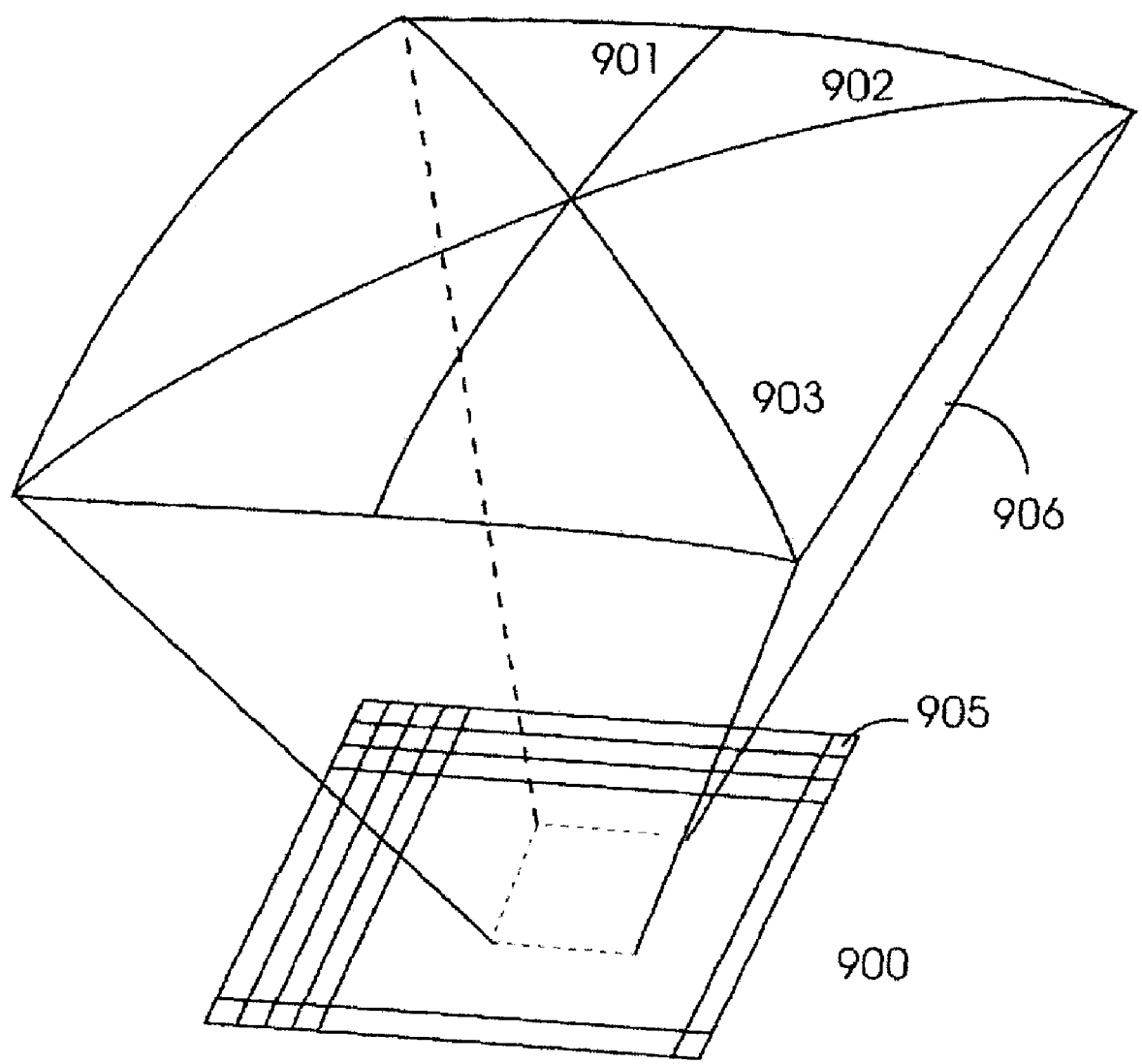
FIG. 9 shows transmission of the ultrasound beam within three selectable 2D scan planes rotated around a common axis with a 2D matrix array.

Electronic steering of the beam within a selected set of 2D scan planes, can also be done with a two-dimensional matrix array illustrated as 900 in FIG. 9. This array is composed of a set of small elements 905 located in a 2D matrix, and where the signal for each element can be individually delayed. By delaying the signals of the individual elements, the beam can be steered and focused in a selected directions within a cone 906, according to known principles. In particular one can select beam directions within a set of 2D scan planes 901, 902, 903 which allows scanning of the ultrasound beam as described above. However, the 2D matrix array severely increases the complexity of the ultrasound scanning system, compared to the arrays in FIGS. 3 and 5.

Figure 10A:
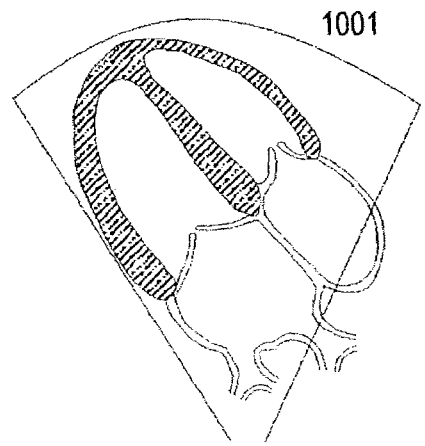
FIG. 10a shows example display of 4 simultaneous, real time 2D images.
Figure 10A:
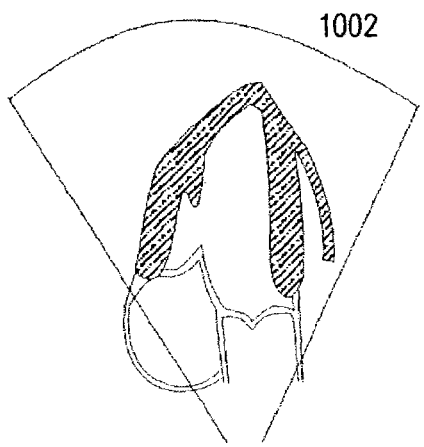
Figure 10A:
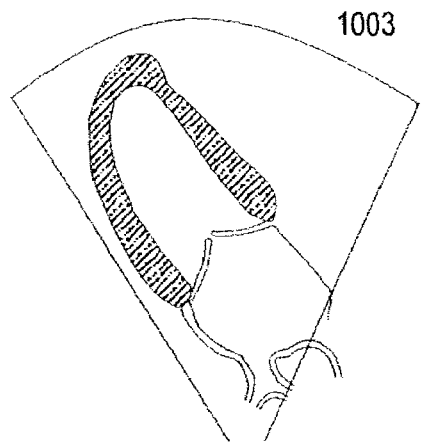
Figure 10A:
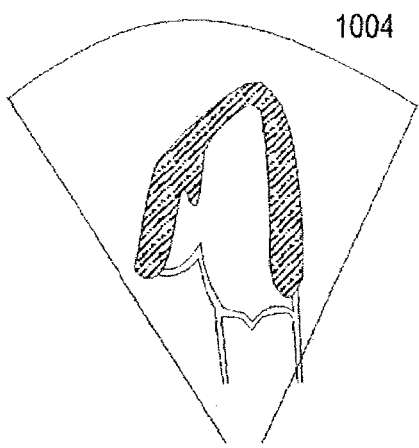
Figure 10A:
Figure 10B:
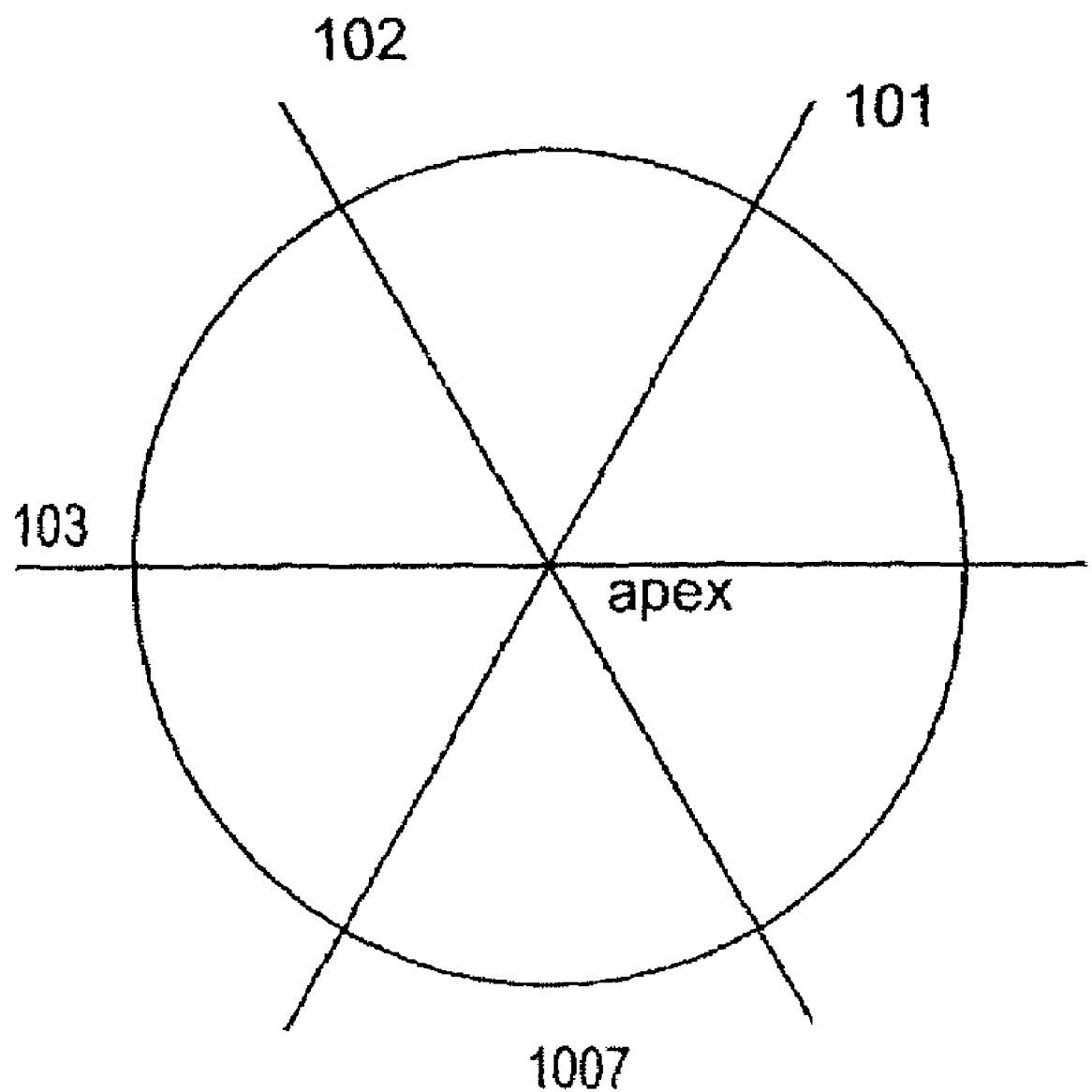
FIG. 10b shows a bullet display of myocardial strain data in three 2D images.

Electronic selection of the 2D scan planes from a set, allows practically simultaneous imaging of the heart in 3 or 4 scan planes with the above described arrays, as discussed in relation to FIG. 1. Here, FIG. 1b shows by way of example a display of real time imaging with three 2D scan planes that for example could be obtained with the array in FIG. 3. Similarly FIG. 10a shows the display of 4 real time scan planes for example obtained with the array in FIG. 5. In this example the 2D image displays 1001-1004 could correspond to the 2D scan planes 601-604 in FIG. 6. A time trace 1005 showing the ECG for timing references, is included in the display together with a region 1006 for display of alphanumeric data, like the end diastolic and end systolic ventricular volumes, the ejection fraction, etc. The images in FIGS. 1a and 10 can typically be used for wall motion scoring, where the score data can be presented in a bullet image, according to well known principles.

Through automatic detection of the ventricular cavities in the 2D images, one can do real time calculation of the volumes of the heart cavities, especially the left ventricle as shown in [6], to study filling and ejection patterns, and also the ejection fraction of the left ventricle. Ultrasound contrast agent can be used to study regional perfusion variations in the myocardium, where harmonic imaging of the contrast agent improves the contrast to tissue power ratio. Ultrasound contrast agent can also be used in difficult to image patients for improved determination of the cavity regions.

In many monitoring situations, a measured left ventricular pressure $p_{LV}(t)$ is available throughout the whole cardiac cycle. In critical situations, like peri and post surgery, $p_{LV}(t)$ can be obtained with a catheter in the left ventricle. In other situations, one can obtain $p_{LV}(t)$ from the aortic pressure throughout systole when the aortic valves are open. The aortic pressure can be obtained from a catheter in a central vessel, or through diameter measurements of the subclavian or carotid vessels. Combined with ultrasound measurements of the left ventricular diameter, D(t), and wall thickness, H(t), one can calculate the fiber stress $\sigma_f(t)$ in the myocardium according to known methods [7] as $$\sigma_f(t) = \frac{H(t)}{(D(t) + H(t))\left(3 - \left(\frac{D(t) + H(t)}{2L(t)}\right)^2\right)} p_{LV}(t) \quad (1)$$

where L(t) is the length of the left ventricular cavity. L(t) can in most situations be approximated by a constant average value. As the myocardial muscle volume is constant, one can also obtain the temporal variations of the wall thickness H(t) from D(T) and L(t). The left ventricular volume $V_{LV}$ can then be approximated by the truncated ellipsoid and calculated based on D(t) and L(t).

There also exists a formula for calculating the fiber stress from the left ventricular cavity volume, $V_{LV}$, and the myocardial wall volume $V_W$ [8] as $$\sigma_f(t) = \frac{3}{\ln\left(1 - \frac{V_W}{V_{LV}(t)}\right)} p_{LV}(t) \quad (2)$$

Such calculations hence allows, according to the invention, real time displays of advanced physiological contraction/relaxation parameters of the myocardium. Temporal differentiation of the parameter wave-forms, including the volume traces, enhances information about the physiological function during the rapid changes at the onset an the end of the contraction.

The average relative strain in the myocardial fibers in a ventricle with close to uniform contraction of the myocardium in all regions, can be approximated as equal to the relative variation in the cardiac diameter, $\omega_a(t)=D(t)/D_{max}$. With regional variations in the strain, as found with ischemic heart disease, the average strain is still an interesting measure of the cardiac performance, but in this situation one would also like to see an image of the regionally variable strain $\omega(r,t)$, where r is a vector coordinate of the of the myocardial surface. Based on Doppler measurements along each beam direction, one can estimate the local strain rate in the myocardium, which can be displayed in different ways, for example as color or grey scale indications in the bullet image 1007 in FIG. 10b, where the angular direction in the bullet image indicates the angular direction of the scan planes of 101, 102, and 103 FIG. 1, and the radial direction in the bullet image indicates the distance from the apex of the heart.

Figure 11:
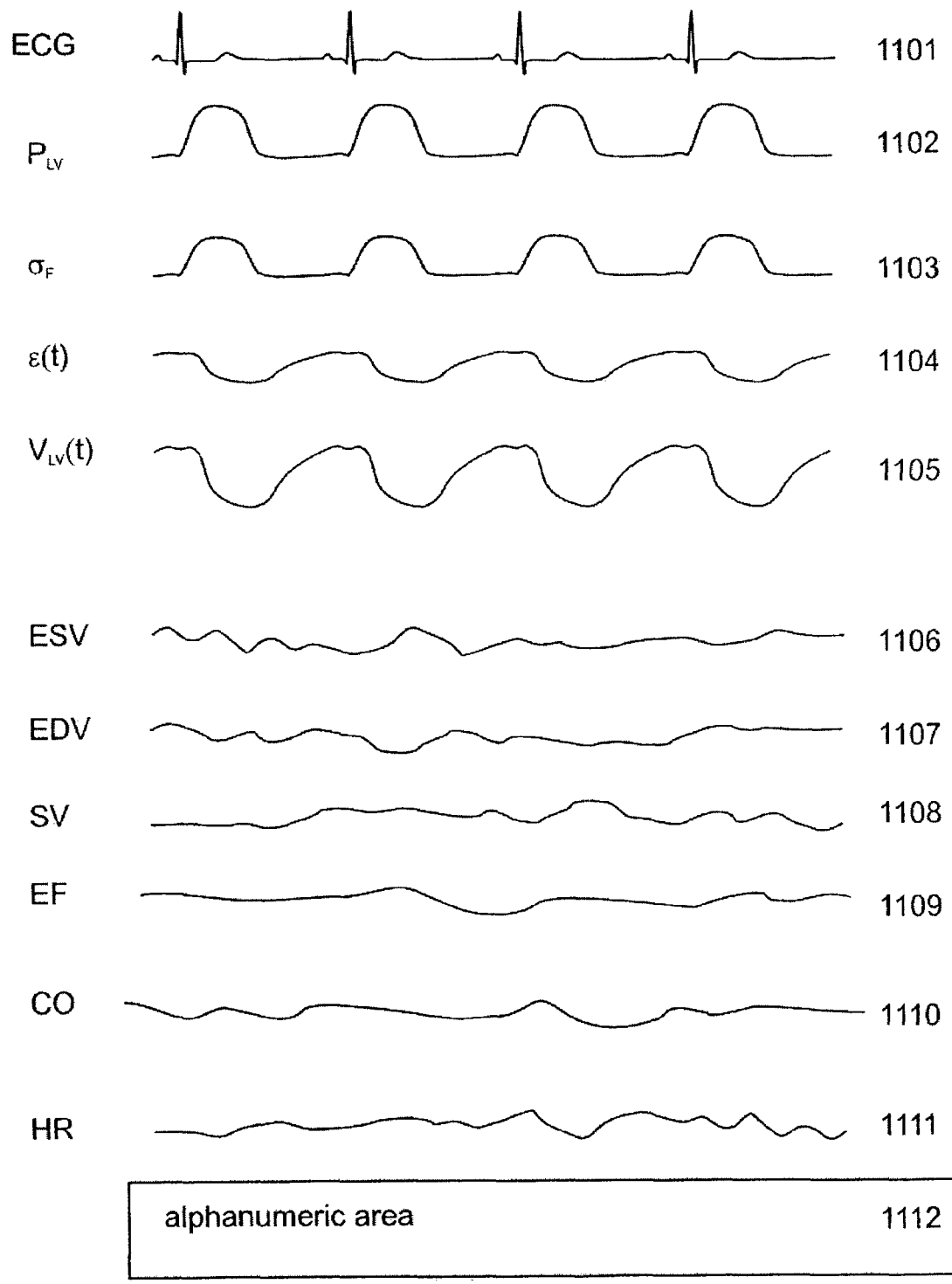
FIG. 11 shows temporal displays of cardiac physiological variables obtained with a cardiac monitoring instrument according to the invention, showing both a fast time which displays variations within a heart beat, and a slow time frame that shows variation of parameters from beat to beat.

To further illustrate the monitoring situation, FIG. 11 shows an example display according to the invention, where the dimensional measurement of the heart obtained with the arrays according to the invention is used to calculate contractile parameters of the left ventricle. The display shows from the top to bottom, the ECG traces 1101, the left ventricular pressure 1102, the fiber stress 1103 and average, relative fiber strain 1104, and the left ventricular volume traces 1105. For trend information over a longer time period, one can show in a slower time scale the end systolic volume, ESV (1106), as the minimum of $V_{LV}$ per beat, the end diastolic volume, EDV (1107), as the maximum of $V_{LV}$ per beat, the stroke volume, SV (1108), cardiac output, EF (1109), and the ejection fraction, CO (1110), calculated as $$SV=EDV-ESV\ CO=SV*HR\ EF=SV/EDV \quad (3)$$

where HR=60/THR is the number of beats per minute calculated from the duration THR of the cardiac cycle per beat in seconds, for example measured for each heart beat from the ECG. These parameters together with HR (1111) and other parameters as for example max(dV/dt), max($\sigma_f$), max($d\sigma_f$/dt), max($\epsilon_a$), max($d\epsilon_a$/dt), etc. can conveniently be displayed as numbers for each heart beat along each trace or in an alphanumeric area 1112.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method for substantially real time ultrasound imaging of an object in one of at least three different 2D image planes, the method comprising the steps of:
   electronically scanning with an ultrasound transducer array a pulsed ultrasound beam along beam directions only within at least three different 2D scan planes, which scan planes intersect along a common axis and are angularly displaced from one another about the common axis, the beam directions being electronically and freely switchable within one of the 2D scan planes or between two of the 2D scan planes from pulse to pulse;
   using the back scattered signal from the pulses in each beam direction to form image data as a function of depth along each beam direction; and
   grouping the image data from the image sample beam directions of each of the scan planes together to form 2D images of the object corresponding to the scan planes, wherein the images are obtained with a high frame rate; whereby substantially real time 2D images from the image data in the at least three different 2D scan planes can be displayed.

2. A method according to claim 1, wherein the ultrasound transducer array allows sector scanning of the ultrasound beam within a fixed number of 2D scan planes, and wherein a particular 2D scan plane of the fixed number of 2D scan planes can be selected electronically with negligible switching time for each transmitted pulse.

3. A method according to claim 1, wherein the at least three different 2D scan planes is three or four different 2D scan planes, the scan planes being uniformly angularly displaced from one another about the common axis.

4. A method according to claim 1, wherein said step of electronically scanning comprises transmitting a wide beam and covering it with multiple receive beams to increase image frame rate.

5. A method according to claim 1, further including the step of reducing the lateral density of transmitted beams in regions of the 2D scan planes in at least one of regions of the 2D scan planes around said common axis, and regions of the 2D scan planes with limited information about the object, to increase an image rate of the scanning.

6. A method according to claim 1, wherein said step of scanning comprises keeping the same scan plane direction for at least a part of a cardiac cycle, and changing to a next one of the scan planes directly before the onset of the myocardial contraction.

7. A method according to claim 1, wherein the transmit and receive apertures are configured so that the width of the ultrasound beam is the same for each 2D scan plane and so that the spatial resolution is the same for each 2D scan planes.

8. A method according to claim 1, including the step of selecting an angle between neighboring 2D scan planes of substantially 60 degrees.

9. A method according to claim 1, including the step of selecting an angle between neighboring 2D scan planes that is different than 60 degrees.

10. A system for ultrasound imaging of an object, the system comprising:
an ultrasound transducer away that allows sector scanning of an ultrasound beam along a direction within at least three different 2D scan planes that are angularly arranged around a common axis so that the 2D scan planes intersect along the common axis, wherein the beam direction can be electronically selected from pulse to pulse, freely between the 2D scan planes or within each 2D scan plane;
the transducer away being connected to an imaging instrument that includes:
means for analyzing a back scattered signal from the ultrasound beam to form image data as a function of depth along the beam direction, and
means for grouping the image data of each of the scan planes to form 2D images of the object corresponding to the at least three 2D scan planes;
means for displaying the 2D images of the object on a common display screen substantially in real time; and
means for selecting a scanning pattern of the ultrasound beam in relation to the number of 2D scan planes and movements of the object so that the ultrasound images can be presented with a high frame rate;
whereby substantially real time imaging of the object in the 2D scan planes is obtained.

11. An ultrasound imaging system according to claim 10, wherein the ultrasound beam is switched to the next one of the 2D scan planes in a rotation direction about the common axis for each sequential beam direction, so that the object is scanned along a spiral conical path with a changing of the beam distance from the common axis as a function of the rotation of the ultrasound beam, for observation of the object with minimal time delays between sampling beams in the 2D scan planes that are similarly spaced from the common axis.

12. An ultrasound imaging system according to claim 10, wherein the object being scanned includes a heart, and the system is used for monitoring cardiac function and the ultrasound imaging system performs at least one cardiac physiological measurement.

13. An ultrasound imaging system according to claim 12, further comprising means for automatic edge detection in the ultrasound images for automatic calculation of at least one of the volume of heart cavities and relative strain in myocardial fibers.

14. An ultrasound imaging system according to claim 13, wherein at least one of ventricular dimensions and ventricular volume are combined with ventricular pressure measurements to calculate the fiber stress in the cavity walls of the heart.

15. An ultrasound imaging system according to either claim 13, wherein simultaneous visualization of the multiple scan planes of the heart is displayed on one of a first part of a first display screen, while temporal variation of parameters derived from the ultrasound images and other physiological measurements are displayed as a function of time on one of at least a second part of the first display screen, and on a second display screen.

16. An ultrasound imaging system according to claim 15, wherein minimum and maximum values of the temporal traces for each cardiac cycle are displayed in a slow time scale.

17. An ultrasound 2D phased array imaging system according to claim 10, in which the ultrasound transducer array is capable of phased array direction steering and focusing of the ultrasound beam within the 2D scan planes, and wherein the array includes:
at least two piezoelectric array layers mounted face to face in a sandwich structure, the sandwich structure having a front direction, a back direction, a front face and a back face;
the back face of the sandwich structure being mounted on a backing material and the front face of the sandwich structure being adapted to be connected to an acoustic load material through at least one elastic layer for acoustic impedance interfacing between the piezoelectric array layers and the load material; and
a set of parallel finger electrodes attached to each face of the piezoelectric away layers, the finger electrodes being electrically isolated from each other, each finger electrode extending in a direction along a row of elements in the piezoelectric away layers, the directions of the sets of finger electrodes on the front face and the back face for each piezoelectric layer forming a non-zero angle with respect to each other;
wherein each set of finger electrodes on the front and back faces is adapted to selectively be connected as one of hot element electrodes to a phased array beam former and a signal ground of the phased array beam former;
whereby selectively connecting the whole set of finger electrodes on one side of at least one piezoelectric array layer as the hot element electrodes to the phased array beam former, and grounding all other sets of finger electrodes on the other faces of the piezoelectric array layers, results in a linear phased array transducer in which the angular direction of the selected 2D scan plane around the common axis is determined by which set of finger electrodes is selected as the hot electrodes of the phased array beam former;

wherein the ultrasound imaging system operates the sets of parallel finger electrodes, and the ultrasound imaging instrument also provides electronic selection signals to control the electronic selection of which set of finger elements is the hot element electrodes, and which sets of finger elements are connected to signal ground, for selection of the ultrasound scan planes for 2D imaging, through one of manual control from the instrument control panel,
automatic selection of the scan planes in a sequence, and
changing the scan plane by a signal derived from an external signal.

18. An ultrasound 2D phased array imaging system according to claim 17 in which the external signal is received from the object.

19. An ultrasound 2D phased array imaging system according to claim 18 in which the external signal is an ECG signal.

20. An ultrasound transducer away capable of phased away direction steering and focusing of an ultrasound beam within a set of at least three electronically selectable 2D scan planes that, are angularly displaced about a common axis along which the 2D scan planes intersect, the away comprising:

at least two piezoelectric array layers mounted face to face in a sandwich structure, the sandwich structure having a front direction, a back direction, a front face and a back face;

the back face of the sandwich structure being mounted on a backing material and the front face of the sandwich structure being adapted to be connected to an acoustic load material through at least one elastic layer for acoustic impedance interfacing between the piezoelectric array layers and the load material; and a set of parallel finger electrodes attached to each face of the piezoelectric away layers, the finger electrodes being electrically isolated from each other, each finger electrode extending in a direction along a row of elements in the piezoelectric away layers, and the directions of the sets of finger electrodes on the front face and the back face for each piezoelectric layer forming a non-zero angle with respect to each other; and wherein each set of finger electrodes on the front and back faces is adapted to selectively be connected as one of hot element electrodes to a phased array beam former and a signal ground of the phased array beam former;

whereby selectively connecting the whole set of finger electrodes on one side of at least one piezoelectric array layer as the hot element electrodes to the phased array beam former, and grounding all other sets of finger electrodes on the other faces of the piezoelectric array layers, causes the away to function as a linear phased away transducer in which the angular direction of the selected 2D scan plane around the common axis is determined by which set of finger electrodes is selected as the hot electrodes of the phased array beam former.

21. An ultrasound transducer array according to claim 20, wherein
the piezoelectric layers are made as a composite of ferroelectric ceramic and polymer;
the composite structure has at least two ceramic posts, and is the same through all piezoelectric array layers in the sandwich structure, and the ceramic posts of the composite structure are separated from each other by at least some linear grooves filled with polymer; and
the linear grooves conform to the separations between the finger electrodes on the face of the piezoelectric layers, and hence also the active phased array elements defined by the electrodes connected to the hot element wires of the beam former.

22. An ultrasound transducer array according to claim 21, wherein
the ceramic posts in the composite structure have a triangular cross section, the triangular cross sections being arranged so that the dicing of the ceramic can be done to form the linear grooves;
some of the linear grooves filled with polymer define the separation between adjacent finger electrodes and hence also the selected, active phased away elements; and
the finger electrodes of one face of each piezoelectric layer each lie in a first direction, while the finger electrodes of the other faces lie in directions that are different for each set of electrodes and different from the first direction.

23. An ultrasound transducer array according to claim 22, wherein
the triangular cross section forms an equilateral triangle, the triangles of each such cross section being arranged so that the dicing of the ceramic can be done in straight lines with a 60° inclination to each other,
the separation of the finger electrodes on the piezoelectric layer surface, conforms with the linear grooves containing polymer in the composite, so that the directions of the finger electrodes form angles of 60° with each other.

24. An ultrasound transducer array according to claim 22, wherein
the piezoelectric layers have opposite polarization directions; and
for operation in a lower frequency band in one 2D scan plane normal to the first direction, the two sets of finger electrodes having the same first direction are connected to each other to form the hot electrodes of a phased array; while the other set of electrodes are coupled to signal ground so that electric parallel operation of the layers is obtained for operation in a lower frequency band; and
for operation in a higher frequency band with the 2D scan plane also normal to the first direction, only the electrodes in one of the front and the back layer lying in the first direction are used as the hot electrodes of the phased array, while all the other sets of finger electrodes are connected to signal ground.

25. An ultrasound transducer array according to claim 20, wherein the directions of the front and back face finger electrodes for each piezoelectric layer form an angle with each other, and the directions of the back finger electrodes of the front piezoelectric layer and the front finger electrodes of the back piezoelectric layer form an angle with respect to each other, so that all the four sets of finger electrodes on the four faces of the piezoelectric layers form non-zero angles with respect to each other.

26. An ultrasound transducer array according to claim 25, wherein the directions of the front and back face finger electrodes for each piezoelectric layer form a 90° angle with respect to each other, and the directions of the back finger electrodes of the front piezoelectric layer and the front finger electrodes of the back piezoelectric layer form an angle of 45° with respect to each other.

27. An ultrasound transducer array according to either claim 21 or 26, wherein the ceramic posts in the composite structure have a cross section of an isosceles triangle with top angles of 90°, the triangles being arranged so that the dicing of the ceramic can be done in straight lines with a 45° inclination with respect to each other.

28. An ultrasound transducer array according to claim 20 for phased away imaging with electronic selection of multiple scan plane directions, wherein
- an electronic switching circuit is mounted close to the transducer array;
- the individual finger electrodes of the electrode sets of each piezoelectric layer face are electrically connected to the electronic switching circuit; and
- the electronic switching circuit is configured to connect the electrode set of one freely selectable face of the piezoelectric layers to the hot wires of the ultrasound beam former while the electrode sets of the other faces of the piezoelectric layers are connected to signal ground.

29. An ultrasound transducer probe composed of an endoscope with an ultrasound away capable of phased array direction steering and focusing of an ultrasound beam within a set of at least three electronically selectable 2D scan planes that are angularly displaced about a common axis along which the 2D scan planes intersect, the array comprising:
- at least two piezoelectric array layers mounted face to face in a sandwich structure, the sandwich structure having a front direction, a back direction, a front face and a back face;
- the back face of the sandwich structure being mounted on a backing material and the front face of the sandwich structure being adapted to be connected to an acoustic load material through at least one elastic layer for acoustic impedance interfacing between the piezoelectric array layers and the load material; and
- a set of parallel finger electrodes attached to each face of the piezoelectric away layers, the finger electrodes being electrically isolated from each other, each finger electrode extending in a direction along a row of elements in the piezoelectric away layers, the directions of the sets of finger electrodes on the front face and the back face for each piezoelectric layer forming a non-zero angle with respect to each other; and
- wherein each set of finger electrodes on the front and back faces is adapted to selectively be connected as one of hot element electrodes to a phased array beam former and a signal ground of the phased array beam former;
- whereby selectively connecting the whole set of finger electrodes on one side of at least one piezoelectric array layer as the hot element electrodes to the phased array beam former, and grounding all other sets of finger electrodes on the other faces of the piezoelectric array layers, results in a linear phased array transducer in which the angular direction of the selected 2D scan plane around the common axis is determined by which set of finger electrodes is selected as the hot electrodes of the phased array beam former;
- wherein the array is mounted at the tip of the endoscope to be inserted into an object for ultrasound imaging of internal structures in the object.

30. An ultrasound transducer probe according to claim 29, wherein the tip of the endoscope is flexible and wherein the flex of the tip can be steered by control at the external end of the endoscope.

31. An ultrasound transducer probe according to claim 29, wherein the away can be rotated in the endoscope tip controlled by one of means positioned at the external end of the endoscope and an imaging instrument.

\* \* \* \* \*